US012603168B2

(12) United States Patent
Murphy et al.

(10) Patent No.: US 12,603,168 B2
(45) Date of Patent: Apr. 14, 2026

(54) SYSTEM, METHOD, AND COMPUTER PROGRAM PRODUCT FOR PROVIDING QUICK RESPONSE (QR) CODES® FOR INJECTION SYSTEMS

(71) Applicant: BAYER HEALTHCARE LLC, Whippany, NJ (US)

(72) Inventors: Steven Murphy, Pittsburgh, PA (US); Dana Horn, Lower Burrell, PA (US); Kumar Gautam, Monroeville, PA (US); Kasinathan Navaneethan, Wexford, PA (US); Swaminathan Balasubramaniam, Monroeville, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 236 days.

(21) Appl. No.: 17/996,673

(22) PCT Filed: May 17, 2021

(86) PCT No.: PCT/US2021/032659
§ 371 (c)(1),
(2) Date: Oct. 20, 2022

(87) PCT Pub. No.: WO2021/236472
PCT Pub. Date: Nov. 25, 2021

(65) Prior Publication Data
US 2023/0238103 A1 Jul. 27, 2023

Related U.S. Application Data

(60) Provisional application No. 62/704,627, filed on May 19, 2020.

(51) Int. Cl.
*G16H 20/17* (2018.01)
*G06K 19/06* (2006.01)

(52) U.S. Cl.
CPC ....... *G16H 20/17* (2018.01); *G06K 19/06037* (2013.01)

(58) Field of Classification Search
CPC ... G16H 20/17; G06K 19/06037; G06K 19/06
See application file for complete search history.

(56) References Cited

U.S. PATENT DOCUMENTS 6,643,537 B1 11/2003 Zatezalo et al.
7,094,216 B2 8/2006 Trombley, III et al.
(Continued)

FOREIGN PATENT DOCUMENTS

CN 110400631 A 11/2019
EP 2923283 A1 9/2015

OTHER PUBLICATIONS

Chu., "Applying QR Code Technology to Facilitate Hospital Medical Equipment Repair Management", 2012 International Conference on Control Engineering and Communication Technology, 2012.

(Continued)

*Primary Examiner* — Kenneth Bartley
(74) *Attorney, Agent, or Firm* — James R. Stevenson; Steven D. Czajkowski; Joseph L. Kent

(57) ABSTRACT

A system for providing a quick response (QR) Code® associated with an injection system is disclosed. The system includes the injection system and at least one processor. The at least one processor is programmed or configured to: receive data associated with the injection system; generate a network resource based on the data associated with the injection system, wherein, when generating the network resource, the at least one processor is programmed or configured to encode the data associated with the injection system into the network resource; generate a QR Code®

(Continued)

100 based on the network resource; and display the QR Code® on a display screen of the injection system.

9 Claims, 12 Drawing Sheets

(56)                References Cited

U.S. PATENT DOCUMENTS

| | | | |
|---|---|---|---|
| 7,457,804 B2 | 11/2008 | Uber, III et al. | |
| 7,556,619 B2 | 7/2009 | Spohn et al. | |
| 7,996,381 B2 | 8/2011 | Uber, III et al. | |
| 8,147,464 B2 | 4/2012 | Spohn et al. | |
| 8,337,456 B2 | 12/2012 | Schriver et al. | |
| 8,521,716 B2 | 8/2013 | Uber, III et al. | |
| 8,540,698 B2 | 9/2013 | Spohn et al. | |
| 9,180,260 B2 | 11/2015 | Huang et al. | |
| 9,329,966 B2 | 5/2016 | Dugan et al. | |
| 9,367,860 B2 | 6/2016 | McKirdy | |
| 9,792,612 B2 | 10/2017 | Dugan et al. | |
| 11,783,928 B2 * | 10/2023 | Abrahamsson | G16H 40/20 |
| | | | 705/3 |
| 2011/0259954 A1 * | 10/2011 | Bartz | G16H 20/17 |
| | | | 235/375 |
| 2012/0239422 A1 * | 9/2012 | Chudy | G07F 11/62 |
| | | | 705/2 |
| 2013/0098983 A1 * | 4/2013 | Neff | G06K 17/0025 |
| | | | 235/375 |
| 2014/0048604 A1 * | 2/2014 | Borges | G06F 16/9554 |
| | | | 235/462.13 |
| 2014/0067426 A1 * | 3/2014 | Neff | G16H 40/63 |
| | | | 705/3 |
| 2014/0092411 A1 | 4/2014 | Burke, Jr. | |
| 2014/0115101 A1 | 4/2014 | Wittner et al. | |
| 2015/0230760 A1 | 8/2015 | Schneider | |
| 2015/0320314 A1 * | 11/2015 | Berger | G06K 7/1417 |
| | | | 340/870.07 |
| 2016/0178479 A1 | 6/2016 | Goldsmith | |
| 2016/0323108 A1 * | 11/2016 | Bhogal | H04W 12/08 |
| 2018/0342317 A1 * | 11/2018 | Skirble | G06K 19/06037 |
| 2019/0065802 A1 * | 2/2019 | Hirschmann | G06K 7/1413 |
| 2019/0328964 A1 * | 10/2019 | Desch | A61M 5/16859 |
| 2020/0364323 A1 * | 11/2020 | Bendersky | G06K 19/06037 |
| 2020/0381106 A1 * | 12/2020 | Limaye | G16H 15/00 |
| 2020/0402622 A1 * | 12/2020 | Ishmael | G06Q 50/22 |
| 2021/0029101 A1 * | 1/2021 | Igari | G06K 7/1417 |
| 2023/0081577 A1 * | 3/2023 | Walker | G16H 40/67 |
| | | | 340/5.81 |
| 2023/0238103 A1 * | 7/2023 | Murphy | H04L 63/0442 |
| | | | 705/2 |

OTHER PUBLICATIONS

"International Preliminary Report on Patentability from PCT Application No. PCT/US2021/032659", Dec. 1, 2022.
Naagaraj; M., "Implementing QR Code Technology in Medical Device Package. Thesis.", 2009.
Niculescu Ms; et al., "LabConcept—A New Mobile Healthcare Platform for Standardizing Patient Results in Telemedicine", Applied Sciences, 2021, 11, 1935.

* cited by examiner

300

302

Receive data associated with an injection system

304

Generate a network resource

306

Generate a Quick Response (QR) code

308

Display the QR code on a display screen

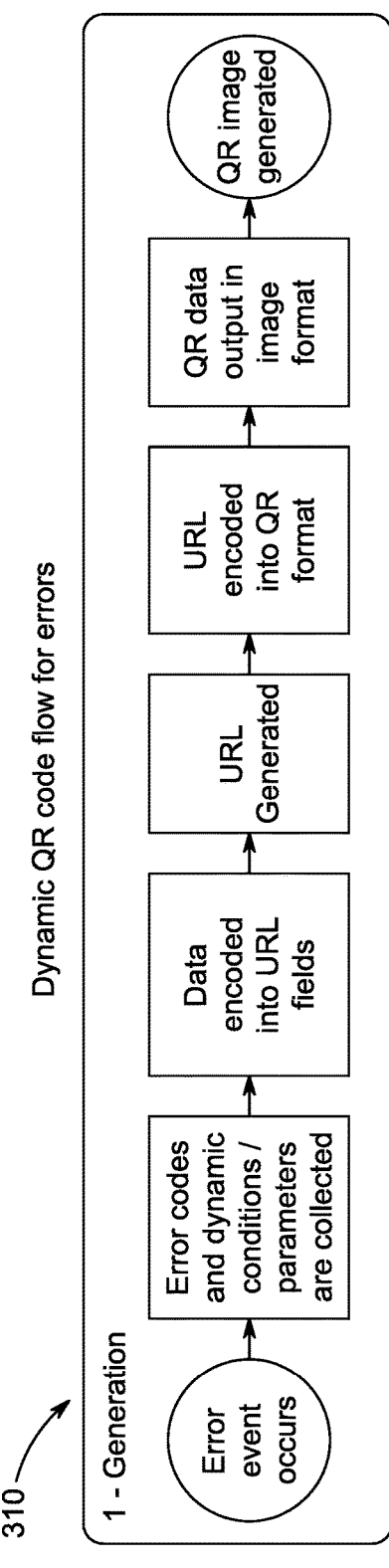

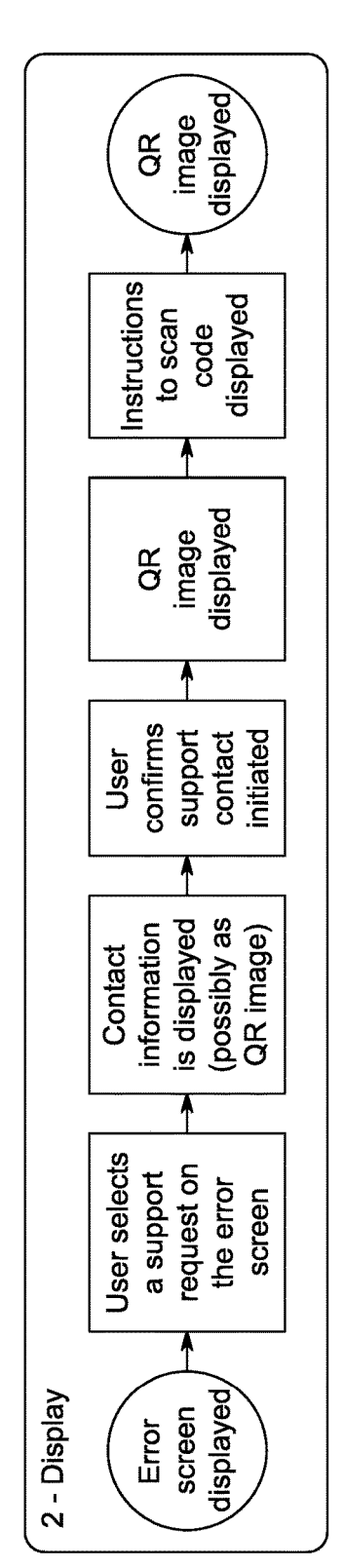

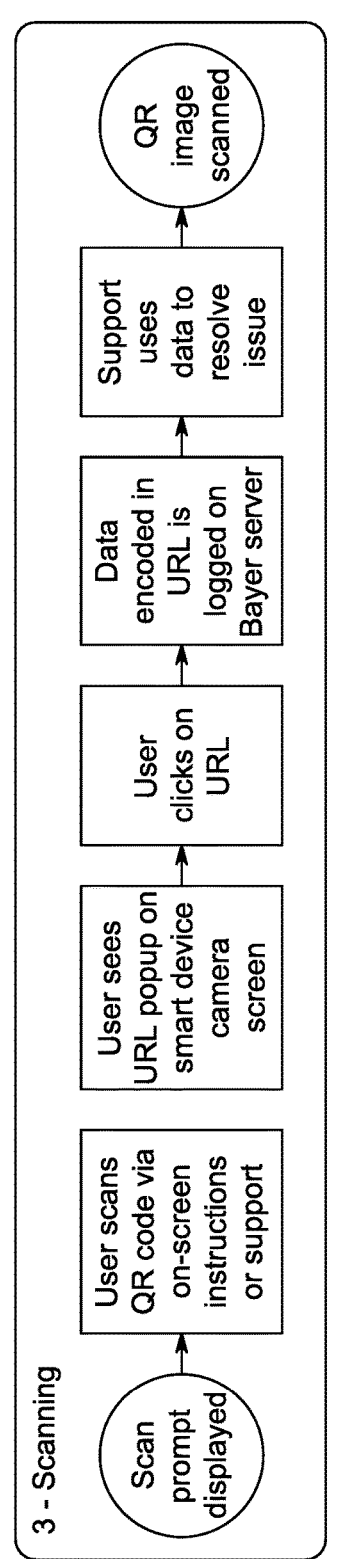

310

Dynamic QR code flow for errors

1 - Generation

Error event occurs → Error codes and dynamic conditions / parameters are collected → Data encoded into URL fields → URL Generated → URL encoded into QR format → QR data output in image format → QR image generated

2 - Display

Error screen displayed → User selects a support request on the error screen → Contact information is displayed (possibly as QR image) → User confirms support contact initiated → QR image displayed → Instructions to scan code displayed → QR image displayed

3 - Scanning

Scan prompt displayed → User scans QR code via on-screen instructions or support → User sees URL popup on smart device camera screen → User clicks on URL → Data encoded in URL is logged on Bayer server → Support uses data to resolve issue → QR image scanned

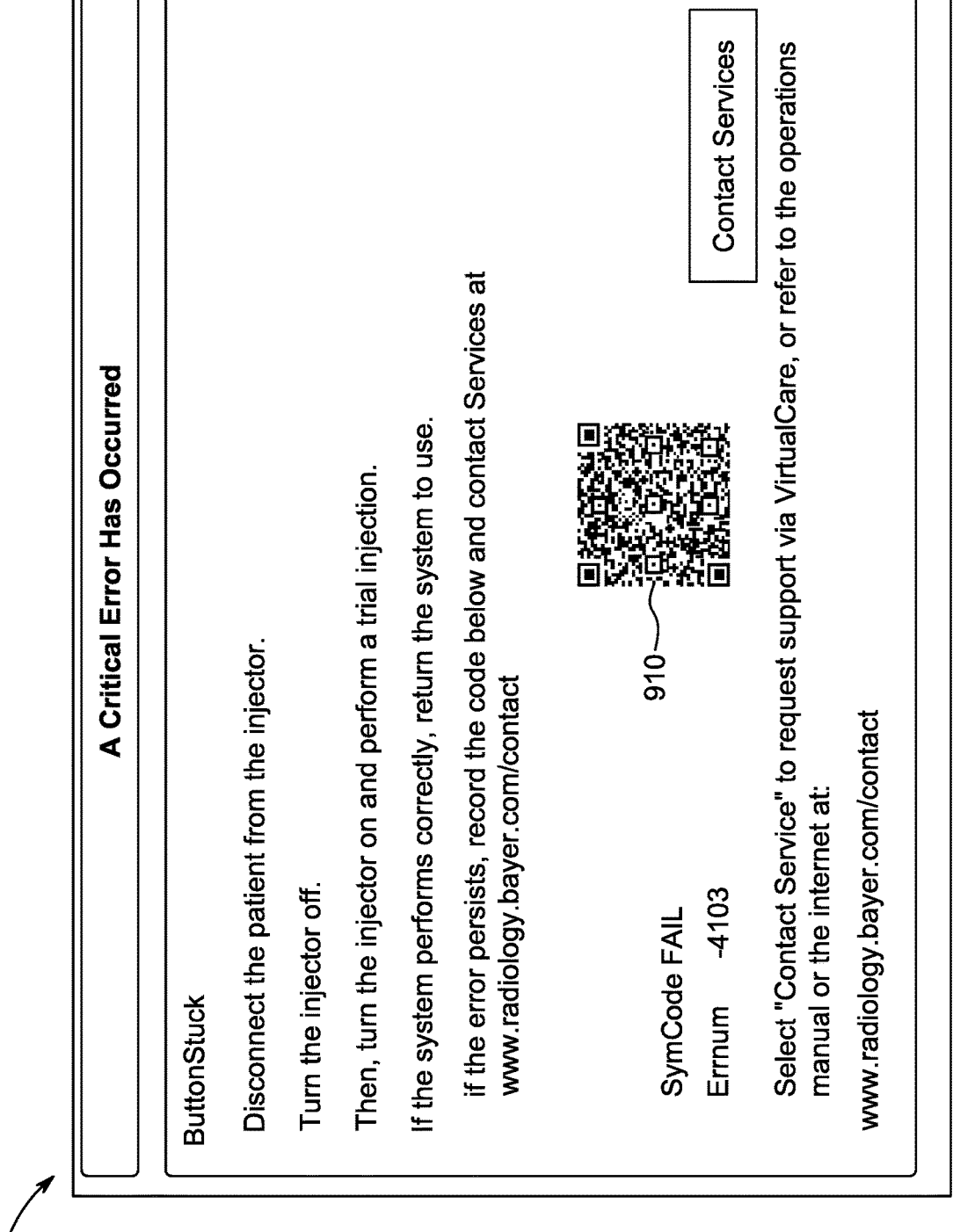

A Critical Error Has Occurred

ButtonStuck

Disconnect the patient from the injector.

Turn the injector off.

Then, turn the injector on and perform a trial injection.

If the system performs correctly, return the system to use.

if the error persists, record the code below and contact Services at www.radiology.bayer.com/contact

910

SymCode FAIL

Errnum   -4103

Contact Services

Select "Contact Service" to request support via VirtualCare, or refer to the operations manual or the internet at:

www.radiology.bayer.com/contact

SYSTEM, METHOD, AND COMPUTER PROGRAM PRODUCT FOR PROVIDING QUICK RESPONSE (QR) CODES® FOR INJECTION SYSTEMS

CROSS-REFERENCE TO RELATED APPLICATIONS

This application is a U.S. national phase application under 35 U.S.C. § 371 of International Application No. PCT/US2021/032659, filed May 17, 2021 and claims the benefit of U.S. Provisional Application No. 62/704,627, filed May 19, 2020, the entire disclosure of which are hereby incorporated by reference in their entirety.

BACKGROUND

1. Field

This disclosure relates generally to systems, devices, products, apparatus, and methods that are used with regard to quick response (QR) Codes®, and in one particular embodiment, to a system, product, and method for providing a QR Code® associated with an injection system.

2. Technical Considerations

An injection device, such as a fluid injection device (e.g., a medical fluid delivery device) may be used by a medical practitioner, such as a physician, in a medical diagnostic procedure and/or a medical therapeutic procedure. For example, the medical practitioner may use the fluid injection device to inject a patient with one or more medical fluids. The fluid injection device may be used for pressurized injection of a medical fluid, such as a radiological contrast material (e.g., a contrast agent, a radiocontrast agent, contrast media, etc.), and/or a flushing agent, such as saline, in medical imaging procedures such as angiography, computed tomography (CT), ultrasound, magnetic resonance imaging (MRI), and positron emission tomography (PET). In some instances, the fluid injection device is designed to deliver a preset amount of a medical fluid at a preset flow rate.

SUMMARY

Accordingly, provided are systems, devices, products, apparatus, and/or methods for providing a quick response (QR) Code® associated with an injection system that improves availability of and/or accessibility to information regarding injection systems.

Further non-limiting embodiments or aspects are set forth in the following numbered clauses:

Clause 1: An injection system for providing a quick response (QR) Code® comprising: at least one processor programmed or configured to: receive data associated with the injection system; generate a network resource based on the data associated with the injection system, wherein, when generating the network resource, the at least one processor is programmed or configured to: encode the data associated with the injection system into the network resource; generate a QR Code® based on the network resource; and display the QR Code® on a display screen of the injection system.

Clause 2: The injection system of clause 1, and wherein the data associated with the injection system comprises data associated with one or more operations of the injection system and wherein the QR Code® comprises a static data element and a dynamic data element; and wherein the static data element comprises data associated with an identifier of the injection system; and wherein the dynamic data element comprises the data associated with one or more operations of the injection system.

Clause 3: The injection system of clause 1 or 2, wherein, when generating the URL, the at least one processor is programmed or configured to: encrypt the network resource.

Clause 4: The injection system of any of clauses 1-3, wherein, when encoding the data associated with the injection system into the network resource, the at least one processor is programmed or configured to: encode data associated with a malfunction encountered during one or more operations of the injection system into the network resource.

Clause 5: The injection system of any of clauses 1-4, wherein, when displaying the QR Code® on the display screen, the at least one processor is programmed or configured to: display the QR Code® on a graphical user interface (GUI) displayed on the display screen of the injection system.

Clause 6: The injection system of any of clauses 1-5, wherein the data associated with the injection system comprises data associated with one or more operations of the injection system; and wherein the at least one processor is further programmed or configured to: log the data associated with one or more operations of the injection system.

Clause 7: The injection system of any of clauses 1-6, wherein the data associated with the injection system comprises: a model number of the injection system; a serial number of the injection system; a software version of the injection system; a revision number of software of the injection system; an identifier of one or more software patches that have been applied to the injection system; a media access control (MAC) address of a network interface controller (NIC) of the injection system; an identifier of an error associated with an operation of the injection system; or any combination thereof; and wherein, when encoding the data associated with the injection system into the network resource, the at least one processor is programmed or configured to: encode, into the network resource, at least one of the following: the model number of the injection system; the serial number of the injection system; the software version of the injection system; the revision number of software of the injection system; the identifier of one or more software patches that have been applied to the injection system; the MAC address of the NIC of the injection system; or the identifier of the error associated with the operation of the injection system.

Clause 8: The injection system of any of clauses 1-7, wherein the network resource comprises a uniform resource locator (URL), and wherein, when generating the network resource, the at least one processor is programmed or configured to: encode the data associated with the injection system into the URL.

Clause 9: The injection system of any of clauses 1-8, wherein, when generating the QR Code®, the at least one processor is programmed or configured to: generate the QR Code® based on the URL.

Clause 10: A system for providing a quick response (QR) Code® associated with an injection system comprising: an injection system; and at least one processor programmed or configured to: receive data associated with the injection system; generate a network resource based on the data associated with the injection system, wherein, when generating the network resource, the at least one processor is programmed or configured to: encode the data associated with the injection system into the network resource; generate a QR Code® based on the network resource; and display the QR Code® on a display screen of the injection system.

Clause 11: The system of clause 10, and wherein the data associated with the injection system comprises data associated with one or more operations of the injection system and wherein the QR Code® comprises a static data element and a dynamic data element; and wherein the static data element comprises data associated with an identifier of the injection system; and wherein the dynamic data element comprises the data associated with one or more operations of the injection system.

Clause 12: The system of clause 10 or 11, wherein, when generating the network resource, the at least one processor is programmed or configured to: encrypt the network resource.

Clause 13: The system of any of clauses 10-12, wherein, when encoding the data associated with the injection system into the network resource, the at least one processor is programmed or configured to: encode data associated with a malfunction encountered during one or more operations of the injection system into the network resource.

Clause 14: The system of any of clauses 10-13, wherein, when displaying the QR Code® on the display screen, the at least one processor is programmed or configured to: display the QR Code® on a graphical user interface (GUI) displayed on the display screen of the injection system.

Clause 15: The system of any of clauses 10-14, wherein the data associated with the injection system comprises data associated with one or more operations of the injection system; and wherein the at least one processor is further programmed or configured to: log the data associated with one or more operations of the injection system.

Clause 16: The system of any of clauses 10-15, wherein the data associated with the injection system comprises: a model number of the injection system; a serial number of the injection system; a software version of the injection system; a revision number of software of the injection system; an identifier of one or more software patches that have been applied to the injection system; a media access control (MAC) address of a network interface controller (NIC) of the injection system; an identifier of an error associated with an operation of the injection system; or any combination thereof; and wherein, when encoding the data associated with the injection system into the network resource, the at least one processor is programmed or configured to: encode, into the network resource, at least one of the following: the model number of the injection system; the serial number of the injection system; the software version of the injection system; the revision number of software of the injection system; the identifier of one or more software patches that have been applied to the injection system; the MAC address of the NIC of the injection system; or the identifier of the error associated with the operation of the injection system.

Clause 17: The system of any of clauses 10-16, wherein the network resource comprises a uniform resource locator (URL), and wherein, when generating the network resource, the at least one processor is programmed or configured to: encode the data associated with the injection system into the URL.

Clause 18: The system of any of clauses 10-17, wherein, when generating the QR Code®, the at least one processor is programmed or configured to: generate the QR Code® based on the URL.

Clause 19: A computer program product for providing a quick response (QR) Code® associated with an injection system, the computer program product comprising at least one non-transitory computer-readable medium comprising one or more instructions that, when executed by at least one processor, cause the at least one processor to: receive data associated with the injection system; generate a network resource based on the data associated with the injection system, wherein, when generating the network resource, the at least one processor is programmed or configured to: encode the data associated with the injection system into the network resource; generate a QR Code® based on the network resource; and display the QR Code® on a display screen of the injection system.

Clause 20: The computer program product of clause 19, and wherein the data associated with the injection system comprises data associated with one or more operations of the injection system and wherein the QR Code® comprises a static data element and a dynamic data element; and wherein the static data element comprises data associated with an identifier of the injection system; and wherein the dynamic data element comprises the data associated with one or more operations of the injection system.

Clause 21: The computer program product of clause 19 or 20, wherein, the one or more instructions that cause the at least one processor to generate the network resource cause the at least one processor to: encrypt the network resource.

Clause 22: The computer program product of any of clauses 19-21, wherein, the one or more instructions that cause the at least one processor to encode the data associated with the injection system into the network resource, cause the at least one processor is to: encode data associated with a malfunction encountered during one or more operations of the injection system into the network resource.

Clause 23: The computer program product of any of clauses 19-22, wherein, the one or more instructions that cause the at least one processor to display the QR Code® on the display screen, cause the at least one processor to: display the QR code on a graphical user interface (GUI) displayed on the display screen of the injection system.

Clause 24: The computer program product of any of clauses 19-23, wherein the data associated with the injection system comprises data associated with one or more operations of the injection system; and wherein the one or more instructions further cause the at least one processor to: log the data associated with one or more operations of the injection system.

Clause 25: The computer program product of any of clauses 19-24, wherein the data associated with the injection system comprises: a model number of the injection system; a serial number of the injection system; a software version of the injection system; a revision number of software of the injection system; an identifier of one or more software patches that have been applied to the injection system; a media access control (MAC) address of a network interface controller (NIC) of the injection system; an identifier of an error associated with an operation of the injection system; or any combination thereof; and wherein, the one or more instructions that cause the at least one processor to encode the data associated with the injection system into the network resource cause the at least one processor to: encode, into the network resource, at least one of the following: the model number of the injection system; the serial number of the injection system; the software version of the injection system; the revision number of software of the injection system; the identifier of one or more software patches that have been applied to the injection system; the MAC address of the NIC of the injection system; or the identifier of the error associated with the operation of the injection system.

Clause 26: The computer program product of any of clauses 19-25, wherein the network resource comprises a uniform resource locator (URL), and wherein, the one or more instructions that cause the at least one processor to generate the network resource cause the at least one processor to: encode the data associated with the injection system into the URL.

Clause 27: The computer program product of any of clauses 19-26, wherein, the one or more instructions that cause the at least one processor to generate the QR Code®, cause the at least one processor to: generate the QR Code® based on the URL.

Clause 28: A method for providing a quick response (QR) Code® associated with an injection system, comprising: receiving, with at least one processor, data associated with an injection system; generating, with the at least one processor, a network resource based on the data associated with the injection system, wherein generating the network resource comprises: encoding the data associated with the injection system into the network resource; generating, with the at least one processor, a QR Code® based on the network resource; and displaying, with the at least one processor, the QR code on a display screen.

Clause 29: The method of clause 28, and wherein the data associated with the injection system comprises data associated with one or more operations of the injection system and wherein the QR Code® comprises a static data element and a dynamic data element; and wherein the static data element comprises data associated with an identifier of the injection system; and wherein the dynamic data element comprises the data associated with one or more operations of the injection system.

Clause 30: The method of clause 28 or 29, wherein generating the network resource comprises: encrypting the network resource.

Clause 31: The method of any of clauses 28-30, wherein encoding the data associated with the injection system into the network resource comprises: encoding data associated with a malfunction encountered during one or more operations of the injection system into the network resource.

Clause 32: The method of any of clauses 28-31, wherein the injection system comprises the display screen, and wherein displaying the QR Code® on the display screen comprises: displaying the QR Code® on the display screen of the injection system.

Clause 33: The method of any of clauses 28-32, wherein the data associated with the injection system comprises data associated with one or more operations of the injection system; and wherein the method further comprising: logging the data associated with one or more operations of the injection system.

Clause 34: The method of any of clauses 28-33, wherein the data associated with the injection system comprises: a model number of the injection system; a serial number of the injection system; a software version of the injection system; a revision number of software of the injection system; an identifier of one or more software patches that have been applied to the injection system; a media access control (MAC) address of a network interface controller (NIC) of the injection system; an identifier of an error associated with an operation of the injection system; or any combination thereof; and wherein encoding the data associated with the injection system into the network resource comprises: encoding, into the network resource, at least one of the following: the model number of the injection system; the serial number of the injection system; the software version of the injection system; the revision number of software of the injection system; the identifier of one or more software patches that have been applied to the injection system; the MAC address of the NIC of the injection system; or the identifier of the error associated with the operation of the injection system.

Clause 35: The method of any of clauses 28-34, wherein the network resource comprises a uniform resource locator (URL), and wherein generating the network resource comprises: encoding the data associated with the injection system into the URL.

Clause 36: The method of any of clauses 28-35, wherein generating the QR Code® comprises: generating the QR Code® based on the URL.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present disclosure. As used in the specification and the claims, the singular form of "a," "an," and "the" include plural referents unless the context clearly dictates otherwise.

BRIEF DESCRIPTION OF THE DRAWINGS

Additional advantages and details of the present disclosure are explained in greater detail below with reference to the exemplary embodiments or aspects that are illustrated in the accompanying schematic figures, in which:

FIG. 3B is a flowchart of an implementation of a process showing how a quick response (QR) Code® may be generated, displayed, and scanned according to a non-limiting embodiment of the present disclosure;

FIG. 9 is a diagram of a non-limiting embodiment of a graphical user interface that includes a QR Code®.

DETAILED DESCRIPTION

Figure 1:
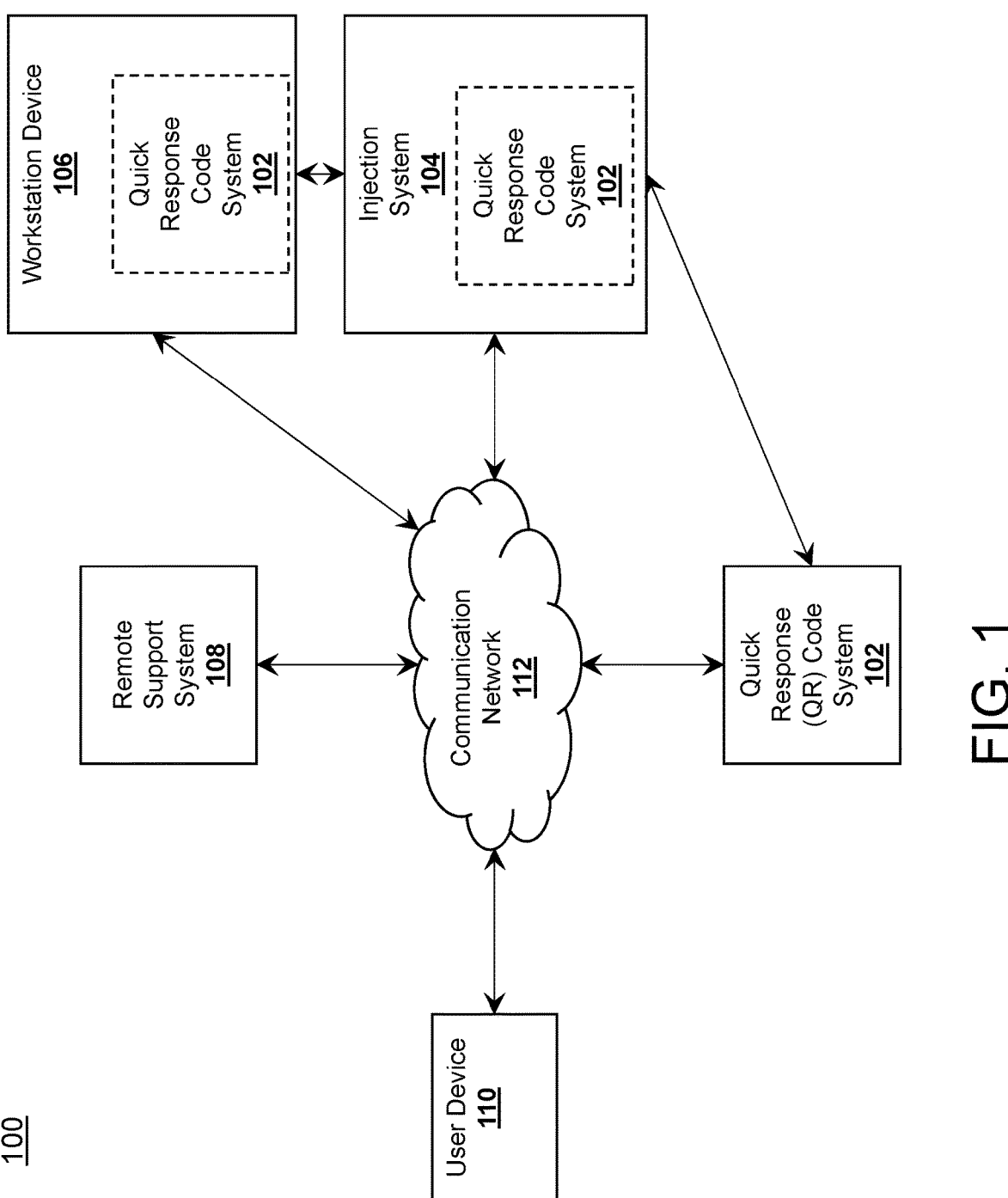
FIG. 1 is a diagram of a non-limiting embodiment or aspect of an environment in which systems, devices, products, apparatus, and/or methods, described herein, may be implemented according to the principles of the present disclosure.

For purposes of the description hereinafter, the terms "end," "upper," "lower," "right," "left," "vertical," "horizontal," "top," "bottom," "lateral," "longitudinal," and derivatives thereof shall relate to the present disclosure as it is oriented in the drawing figures. However, it is to be understood that the present disclosure may assume various alternative variations and step sequences, except where expressly specified to the contrary. It is also to be understood that the specific devices and processes illustrated in the attached drawings, and described in the following specification, are simply exemplary embodiments or aspects of the present disclosure. Hence, specific dimensions and other physical characteristics related to the embodiments or aspects of the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments, a message may refer to a network packet (e.g., a data packet and/or the like) that includes data. It will be appreciated that numerous other arrangements are possible.

As used herein, the term "system" may refer to one or more computing devices or combinations of computing devices such as, but not limited to, processors, servers, client devices, software applications, and/or other like components. In addition, reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

In some instances, a fluid injection system may be part of a group of devices that are used in a medical treatment facility, such as a hospital, during treatment of patients. However, during operation of the fluid injection system, information regarding the fluid injection system may not be readily available. For example, the fluid injection system may malfunction during a fluid injection operation and information regarding the malfunction may not be readily available to either the users of the fluid injection system or support staff that are tasked with providing technical support for the fluid injection system. Additionally, the fluid injection system may not be able to display an appropriate amount of information for a user to understand details regarding the malfunction. For example, a display screen of the fluid injection system may only contain a limited amount of space for displaying information to the user. Furthermore, a user may encounter difficulty when attempting to relay information regarding the malfunction to technical support.

In some non-limiting embodiments, a quick response (QR) Code® may include a type of matrix barcode (e.g., a two-dimensional barcode) that is a machine-readable optical label that includes information about an object (e.g., an object to which the QR Code® is attached). In some non-limiting embodiments, a QR Code® may include data associated with a locator, an identifier, or a tracker that points to a website and/or an application. A QR Code® may use four standardized encoding modes (numeric, alphanumeric, byte/binary, and kanji) to store data. Additionally, a QR Code® may consist of black squares arranged in a square grid on a white background, which can be read by a reader device, such as a camera. An image received by the reader device based on reading the QR Code® may be processed using Reed-Solomon error correction until the image of the QR Code® can be appropriately interpreted. The data encoded in the QR Code® may be extracted based on patterns that are present in horizontal components and/or vertical components of the image.

Non-limiting embodiments or aspects of the present disclosure are directed to systems, devices, products, apparatus, and/or methods for providing a quick response (QR) Code® associated with an injection system. In some non-limiting embodiments, a QR Code® system may include an injection system and at least one processor programmed or configured to: receive data associated with the injection system; generate a uniform resource locator (URL) based on the data associated with the injection system, wherein, when generating the URL, the at least one processor is programmed or configured to: encode the data associated with the injection system into one or more fields of the URL; generate a QR Code® based on the URL; and display the QR Code® on a display screen of the injection system. In some non-limiting embodiments, the QR Code® comprises a static data element and a dynamic data element; and the static data element comprises data associated with an identifier of the injection system; and the dynamic data element comprises the data associated with one or more operations of the injection system. In some non-limiting embodiments, when generating the URL, the at least one processor is programmed or configured to: encrypt the one or more fields of the URL. In some non-limiting embodiments, when encoding the data associated with the injection system into one or more fields of the URL, the at least one processor is programmed or configured to: encode data associated with a malfunction encountered during one or more operations of the injection system into one or more fields of the URL. In some non-limiting embodiments, when displaying the QR Code® on the display screen, the at least one processor is programmed or configured to: display the QR Code® on a graphical user interface (GUI) displayed on the display screen of the injection system. In some non-limiting embodiments, the data associated with the injection system comprises data associated with one or more operations of the injection system; and the at least one processor is further programmed or configured to: log the data associated with one or more operations of the injection system. In some non-limiting embodiments, the data associated with the injection system comprises: a model number of the injection system; a serial number of the injection system; a software version of the injection system; a revision number of software of the injection system; an identifier of one or more software patches that have been applied to the injection system; a media access control (MAC) address of a network interface controller (NIC) of the injection system; an identifier of an error associated with an operation of the injection system; or any combination thereof; and wherein, when encoding the data associated with one or more operations of the injection system into one or more fields of the URL, the at least one processor is programmed or configured to: encode, into one or more fields of the URL, at least one of the following: the model number of the injection system; the serial number of the injection system; the software version of the injection system; the revision number of software of the injection system; the identifier of one or more software patches that have been applied to the injection system; the MAC address of the NIC of the injection system; or the identifier of the error associated with the operation of the injection system.

In this way, non-limiting embodiments of the present disclosure provide for readily available access to information regarding a fluid injection system. In particular, when the fluid injection system malfunctions during a fluid injection operation, information regarding the malfunction may be readily available via a QR Code® to the users of the fluid injection system and/or personnel that provide support services for the fluid injection system. Additionally, the information regarding the malfunction may be provided to users of the fluid injection system and/or personnel that provide support services for the fluid injection system via a URL, from which the QR Code® is based on, so that the details regarding the malfunction may be understood. Additionally, information regarding the malfunction of fluid injection system may be more accurately provided as compared to a user attempting to relay information regarding the malfunction to the personnel that provide support services. Further, a user of the fluid injection system will not be required to keep tedious physical records regarding many aspects of the fluid injection system, including warranty information, license information, service history records, and/or the like.

Referring now to FIG. 1, FIG. 1 is a diagram of an example environment 100 in which devices, systems, and/or methods, described herein, may be implemented. As shown in FIG. 1, environment 100 includes quick response (QR) Code® system 102, injection system 104, workstation device 106, remote support system 108, user device 110, and communication network 112. In some non-limiting embodiments, QR Code® system 102, injection system 104, workstation device 106, remote support system 108, and/or user device 110 may interconnect (e.g., establish a connection to communicate) via wired connections, wireless connections, or a combination of wired and wireless connections.

In some non-limiting embodiments, QR Code® system 102 includes one or more devices capable of being in communication with injection system 104, workstation device 106, remote support system 108, and/or user device 110 via communication network 112. For example, QR Code® system 102 can include a computing device, such as a computer, a server, a group of servers, and/or other like devices. In some non-limiting embodiments, QR Code® system 102 may be configured to receive data associated with an injection system (e.g., injection system 104), generate a uniform resource locator (URL), and/or generate a QR Code® based on the URL. In some non-limiting embodiments, QR Code® system 102 may be a component of injection system 104 and/or workstation device 106.

In some non-limiting embodiments, injection system 104 includes one or more devices capable of being in communication with QR Code® system 102, workstation device 106, remote support system 108, and/or user device 110 via communication network 112. For example, injection system 104 can include a computing device, such as one or more computers, a server, a group of servers, and/or other like devices. In some non-limiting embodiments, injection system 104 includes one or more injection devices (e.g., one or more fluid injection devices). In some non-limiting embodiments, injection system 104 is configured to administer (e.g., inject, deliver, etc.) contrast fluid including a contrast agent to a patient, and/or administer an aqueous fluid, such as saline, to a patient before, during, and/or after administering the contrast fluid. For example, injection system 104 can inject one or more prescribed dosages of contrast fluid directly into a patient's blood stream via a hypodermic needle and syringe. In some non-limiting embodiments, injection system 104 may be configured to continually administer the aqueous fluid to a patient through a peripheral intravenous line (PIV) and catheter, and one or more prescribed dosages of contrast fluid may be introduced into the PIV and administered via the catheter to the patient. In some non-limiting embodiments, injection system 104 is configured to inject a dose of contrast fluid followed by administration of a particular volume of the aqueous fluid.

In some non-limiting embodiments, injection system 104 may include one or more exemplary injection systems or injectors that are disclosed in: U.S. patent application Ser. No. 09/715,330, filed on Nov. 17, 2000, issued as U.S. Pat. No. 6,643,537; U.S. patent application Ser. No. 09/982,518, filed on Oct. 18, 2001, issued as U.S. Pat. No. 7,094,216; U.S. patent application Ser. No. 10/825,866, filed on Apr. 16, 2004, issued as U.S. Pat. No. 7,556,619; U.S. patent application Ser. No. 12/437,011, filed May 7, 2009, issued as U.S. Pat. No. 8,337,456; U.S. patent application Ser. No. 12/476,513, filed Jun. 2, 2009, issued as U.S. Pat. No. 8,147,464; and U.S. patent application Ser. No. 11/004,670, filed on Dec. 3, 2004, issued as U.S. Pat. No. 8,540,698, the disclosures of each of which are incorporated herein by reference in their entireties. In some non-limiting embodiments, injection system 104 may include the MEDRAD® Stellant CT Injection System, the MEDRAD® Stellant Flex CT Injection System, the MEDRAD® MRXperion MR Injection System, the MEDRAD® Mark 7 Arterion Injection System, the MEDRAD® Intego PET Infusion System, or the MEDRAD® Centargo CT Injection System, all of which are provided by Bayer.

In some non-limiting embodiments, workstation device 106 includes one or more devices capable of being in communication with QR Code® system 102, injection system 104, remote support system 108, and/or user device 110 via communication network 112. For example, workstation device 106 may include a computing device, such as one or more computers, including a desktop computer, a laptop, a tablet, and/or the like. In some non-limiting embodiments, workstation device 106 may provide a control interface for controlling operation of injection system 104, including providing inputs to injection system 104. Additionally or alternatively, workstation device 106 may display operational parameters of injection system 104 during operation (e.g., during real-time operation) of injection system 104. In some non-limiting embodiments, workstation device 106 may provide interconnectivity between injection system 104 and other devices or systems, such as a scanner device (not shown). In some non-limiting embodiments, workstation device 106 may include the Certegra® Workstation provided by Bayer.

In some non-limiting embodiments, remote support system 108 may include one or more devices capable of being in communication with QR Code® system 102, injection system 104, workstation device 106, and/or user device 110 via communication network 112. For example, remote system 108 may include a computing device, such as a computer, a server (e.g., a web server), a group of servers, and/or other like devices. In some non-limiting embodiments, remote support system 108 may include a back-end system associated with QR Code® system 102, injection system 104, and/or workstation device 106. In some non-limiting embodiments, remote support system 108 may include a cloud computing system that stores data in an associated database. In some non-limiting embodiments, remote support system 108 may be capable of interacting with injection system 104 to provide functionality, such as remote equipment service for injection system 104 (e.g., VirtualCARE® remote equipment support service for injection systems and devices provided by Bayer). In some non-limiting embodiments, remote support system 108 may be operated by or on behalf of an original equipment manufacturer (OEM) of injection system 104 (e.g., an OEM of one or more components or devices of injection system 104), a provider of injection system 104, an imaging site or a hospital in which injection system 104 is operated, a service technician assigned to injection system 104, and/or the like.

In some non-limiting embodiments, user device 110 may include one or more devices capable of being in communication with QR Code® system 102, injection system 104, workstation device 106, and/or remote support system 108 via communication network 112. For example, user device 110 may include a computing device, such as a computer, including a desktop, a laptop, a tablet, a mobile device, such as a smartphone, and/or the like. In some non-limiting embodiments, user device 110 may be capable of reading (e.g., scanning) a barcode, such as a QR Code®.

In some non-limiting embodiments, communication network 112 may include one or more wired and/or wireless networks. For example, communication network 112 may include a cellular network (e.g., a long-term evolution (LTE) network, a third generation (3G) network, a fourth generation (4G) network, a fifth generation (5G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, a short range wireless communication network (e.g., a Bluetooth network, a near field communication (NFC) network, etc.) and/or the like, and/or a combination of these or other types of networks.

The number and arrangement of systems, devices, and networks shown in FIG. 1 are provided as an example. There may be additional systems and/or devices, fewer systems and/or devices, different systems and/or devices, and/or differently arranged systems and/or devices than those shown in FIG. 1. Furthermore, two or more systems or devices shown in FIG. 1 may be implemented within a single system or a single device, or a single system or a single device shown in FIG. 1 may be implemented as multiple, distributed systems or devices. Additionally, or alternatively, a set of systems or a set of devices (e.g., one or more systems, one or more devices, etc.) of environment 100 may perform one or more functions described as being performed by another set of systems or another set of devices of environment 100.

Figure 2:
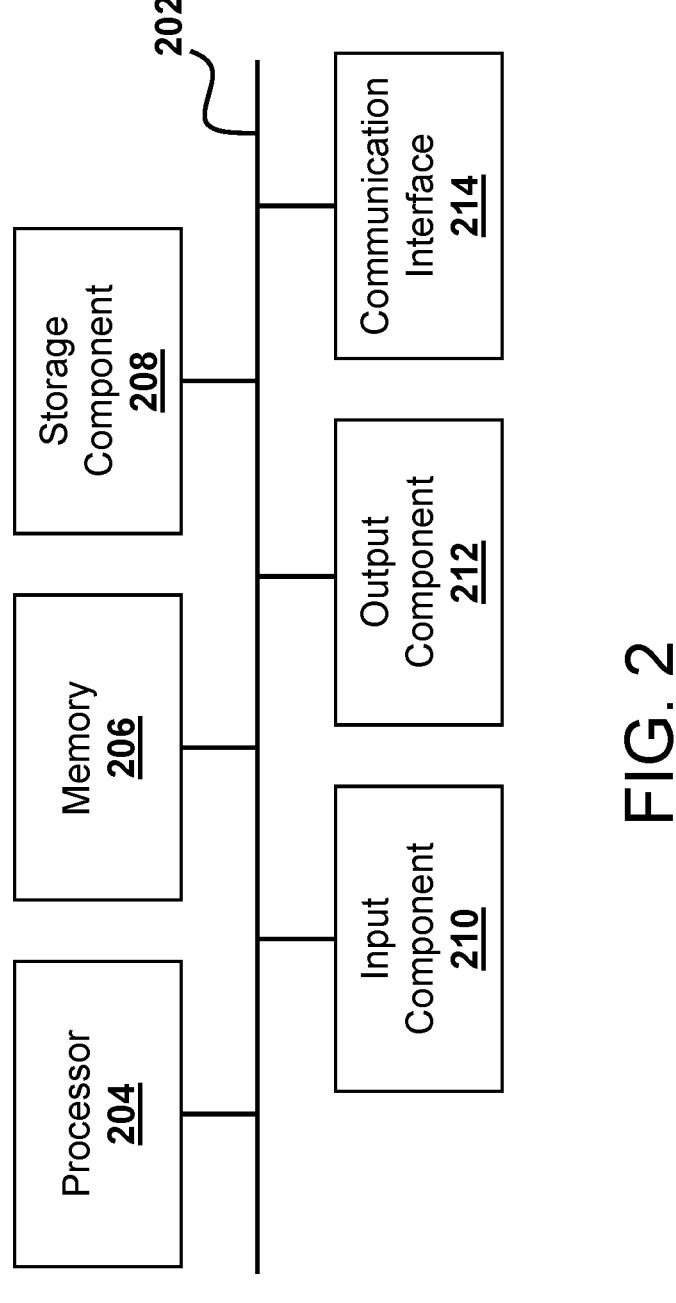
FIG. 2 is a diagram of a non-limiting embodiment or aspect of components of one or more systems or one or more devices of FIG. 1.

Referring now to FIG. 2, FIG. 2 is a diagram of example components of a device 200. Device 200 may correspond to one or more devices of QR Code® system 102, one or more devices of injection system 104, workstation device 106, one or more devices of remote support system 108, and/or user device 110. In some non-limiting embodiments, QR Code® system 102, injection system 104, workstation device 106, remote support system 108, and/or user device 110 can include at least one device 200 and/or at least one component of device 200. As shown in FIG. 2, device 200 may include bus 202, processor 204, memory 206, storage component 208, input component 210, output component 212, and communication interface 214.

Bus 202 may include a component that permits communication among the components of device 200. In some non-limiting embodiments, processor 204 may be implemented in hardware, software, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read only memory (ROM), and/or another type of dynamic or static storage device (e.g., flash memory, magnetic memory, optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally, or alternatively, input component 210 may include a sensor for sensing information (e.g., a global positioning system (GPS) component, an accelerometer, a gyroscope, an actuator, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmitter, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally, or alternatively, hardwired circuitry may be used in place of or in combination with software instructions to perform one or more processes described herein. Thus, embodiments or aspects described herein are not limited to any specific combination of hardware circuitry and software.

The number and arrangement of components shown in FIG. 2 are provided as an example. In some non-limiting embodiments, device 200 may include additional components, fewer components, different components, or differently arranged components than those shown in FIG. 2. Additionally or alternatively, a set of components (e.g., one or more components) of device 200 may perform one or more functions described as being performed by another set of components of device 200.

Figure 3A:
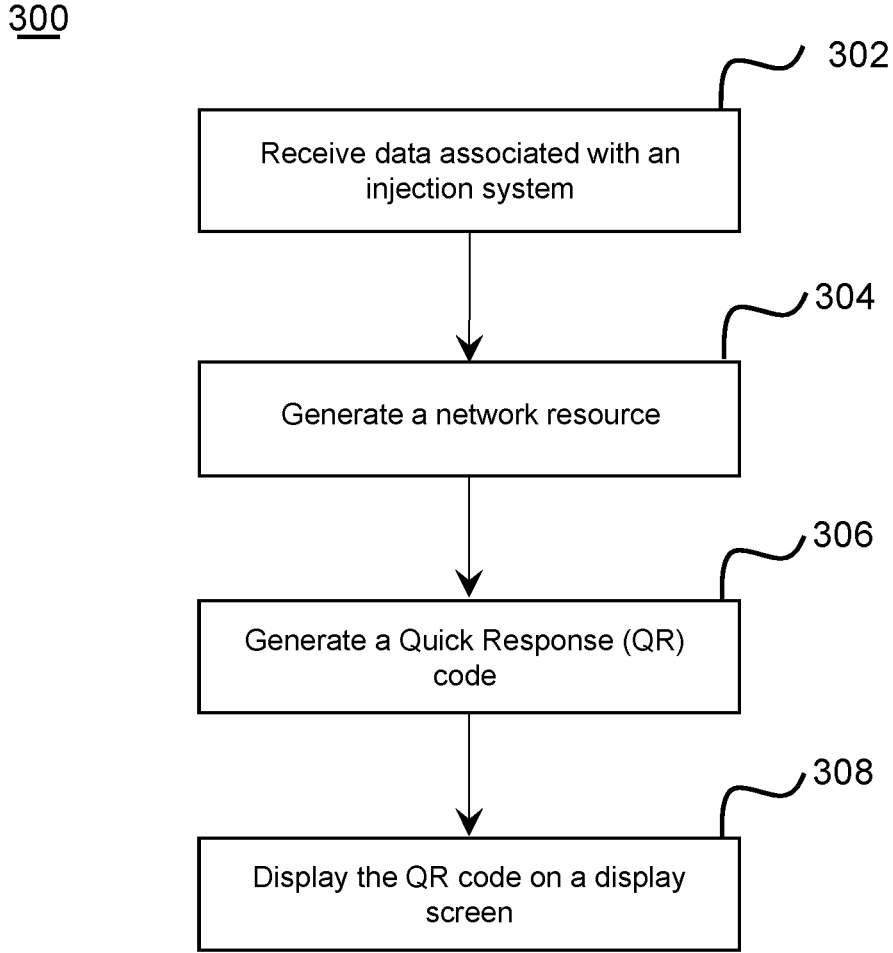
FIG. 3A is a flowchart of a non-limiting embodiment of a process for predictive maintenance.

Referring now to FIG. 3A, FIG. 3A is a flowchart of a non-limiting embodiment or aspect of a process 300 for providing a QR Code® associated with an injection system. In some non-limiting embodiments, one or more of the steps of process 300 are performed (e.g., completely, partially, etc.) by QR Code® system 102 (e.g., one or more devices of QR Code® system 102, etc.). In some non-limiting embodiments, one or more of the steps of process 300 are performed (e.g., completely, partially, etc.) by another device or a group of devices separate from or including QR Code® system 102, such as injection system 104 (e.g., one or more devices of injection system 104, etc.), workstation device 106, remote support system 108 (e.g., one or more devices of remote support system 108, etc.), and/or user device 110. Aspects of non-limiting embodiments herein may be described with regard to uniform resource locator (URL). According to some non-limiting embodiments, a uniform resource indicator (URI) may be substituted for a URL where a URL is described.

As shown in FIG. 3A, at step 302, process 300 includes receiving data associated with an injection system. For example, QR Code® system 102 may receive data associated with injection system 104. In some non-limiting embodiments, QR Code® system 102 may receive the data associated with injection system 104 from injection system 104, workstation device 106, remote support system 108, user device 110, and/or one or more other devices associated with an operation, a medical procedure, a patient, and/or a user or operator associated with injection system 104 (e.g., a power supply system, an imaging device or scanner, such as a computed tomography (CT) system, a magnetic resonance imaging (MRI) system, and/or the like, a patient device, such as a patient identification device (e.g., a wearable radio frequency identification (RFID) tag and/or a computing device, etc.). In some non-limiting embodiments, QR Code® system 102 may receive data associated with injection system 104 continuously, periodically, and/or based on an action performed with regard to injection system 104, such as receiving a user request for an operation to be performed by injection system 104, a diagnostic operation to be performed by injection system 104, a benchmarking service performed by injection system 104, a startup (e.g., a boot-up, turning on, powering up, etc.) operation performed by injection system 104, and/or a shut-down (e.g., a turning off, powering down, etc.) of injection system 104. In some non-limiting embodiments, QR Code® system 102 may receive the data associated with injection system 104 by retrieving the data associated with injection system 104 from a memory of injection system 104, workstation device 106, remote support system 108 (e.g., a cloud data storage location of remote support system 108), and/or the like. In some non-limiting embodiments, QR Code® system 102 may remove specific data from the data associated with injection system 104 using a log scrubber. For example, QR Code® system 102 may remove sensitive data (e.g., sensitive personal data such as, but not limited to, protected health information (PHI), personally identifiable information (PII), etc.) from the data associated with injection system 104 using a log scrubber.

In some non-limiting embodiments, the data associated with injection system 104 may include data associated with identification of injection system 104. For example, the data associated with injection system 104 may include data associated with an identifier of injection system 104 (e.g., a device identifier of injection system 104, such as a model number of injection system 104, a serial number of injection system 104, etc.), data associated with software or hardware of injection system 104 (e.g., a software configuration of injection system 104, a hardware configuration of injection system 104, a software version of injection system 104, such as a software version of an operating system of injection system 104, a revision number of software of injection system 104, an identifier of one or more software patches that have been applied to injection system 104, etc.), and/or data associated with a network connection of injection system 104 (e.g., a media access control (MAC) address of a network interface controller (NIC) of injection system 104, an Internet Protocol (IP) address of injection system 104, etc.). In some non-limiting embodiments, the data associated with injection system 104 may include data associated with one or more operations of injection system 104. The data associated with one or more operations of injection system 104 may include data associated with operations carried out by injection system 104 (e.g., a number of fluid injection operations carried out by injection system 104, times of fluid injection operations carried out by injection system 104, operational parameters of fluid injection operations carried out by injection system 104, data associated with patient demographics for patients upon which fluid injection operations were carried out by injection system 104, etc.), data associated with a configuration of injection system 104 (e.g., a configuration of fluid delivery components of injection system 104, a cybersecurity bill of materials (CBOM) of injection system 104), and/or data associated with a malfunction encountered during one or more operations of injection system 104. In some non-limiting embodiments, QR Code® system 102 may log (e.g., store in a data log) the data associated with injection system 104. For example, QR Code® system 102 may log the data associated with one or more operations of injection system 104. It is noted that embodiments of the present disclosure comply with all legal requirements, for example, the Health Insurance Portability and Accountability Act (HIPAA), such that data associated with injection system 104 that is stored or communicated may not include personal health information of patients, such as PHI and PII, as appropriate.

In some non-limiting embodiments, operational parameters of fluid injection operations carried out by injection system 104 may include one or more exemplary data types that are disclosed in U.S. patent application Ser. No. 10/143,562, filed on May 10, 2002, issued as U.S. Pat. No. 7,457,804; U.S. patent application Ser. No. 12/254,318, filed on Oct. 20, 2008, issued as U.S. Pat. No. 7,996,381; U.S. patent application Ser. No. 13/180,175, filed on Jul. 11, 2011, issued as U.S. Pat. No. 8,521,716, the disclosures of each of which are incorporated herein by reference in their entireties.

In some non-limiting embodiments, the data associated with a malfunction encountered during one or more operations of injection system 104 may include an identifier of an error associated with an operation of injection system 104. The identifier of the error associated with the operation of injection system 104 may include an error code (e.g., a specific error code associated with the type of malfunction encountered). Additionally or alternatively, the data associated with a malfunction encountered during one or more operations of injection system 104 may include operational parameters of injection system 104 associated with the malfunction. For example, the data associated with a malfunction encountered during one or more operations of injection system 104 may include a temperature measurement of a component of injection system 104, a measurement of an electrical characteristic (e.g., voltage, current, power, etc.) of electrical components of injection system 104, and/or other relevant values of variables and/or system components.

As further shown in FIG. 3A, at step 304, process 300 includes generating a network resource. For example, QR Code® system 102 may generate a network resource (e.g., a secure network resource) based on the data associated with injection system 104. In some non-limiting embodiments, the network resource may include a uniform resource locator (URL) (e.g., a secure URL), an email, a messaging service message (e.g., a short message service (SMS) message, a text message, etc.), a file on a network system, and/or the like. In some non-limiting embodiments, QR Code® system 102 may generate (e.g., automatically generate) the network resource based on receiving the data associated with injection system 104. In some non-limiting embodiments, QR Code® system 102 may generate the network resource based on receiving a request (e.g., a user request) to generate a QR Code® or a request to generate the network resource.

In some non-limiting embodiments, the network resource may include a URL and the URL may include a link to a service. For example, the URL may include a link to a service that allows a user to obtain equipment service from technical support for injection system 104, a service that allows a user to retrieve documentation associated with injection system 104, a service that allows for uploading data associated with injection system 104 (e.g., data associated with product and/or warranty registration of injection system 104, such as a model number of injection system 104, a serial number of injection system 104, a date of purchase of injection system 104, and/or the like, data associated with a license of features for injection system 104, such as data associated with a license renewal application of features for injection system 104, etc.) to a location (e.g., a secure server location associated with remote support system 108), and/or the like. In some non-limiting embodiments, the URL may include a link to a website (e.g., a webpage of a website) that includes device-specific files for injection system 104, such as product documentation data files (e.g., user manuals, user instructions for operations, training videos, feature order forms, work orders, part numbers, software versions, licenses, such as software licenses, etc.), sales documentation data files (e.g., invoices, warranty documents, service plan documents, etc.), and/or service history documentation data files (e.g., documents that describe prior maintenance services and/or repair services performed, installation documents, etc.). In some non-limiting embodiments, the URL may include a link to remote support system 108. For example, the URL may include a link to an entity of remote support system 108 that provides equipment service for injection system 104. In some non-limiting embodiments, the URL may include a link to an Enterprise Resource Planning (ERP) system (e.g., an ERP system associated with remote support system 108). In some non-limiting embodiments, the URL may include a link to a specific application and/or service (e.g., web service) that performs a function, such as performing a function for locating injection system 104.

In some non-limiting embodiments, QR Code® system 102 may encode the data associated with injection system 104 into one or more fields (e.g., into one or more values of one or more fields) of the network resource (e.g., a URL). For example, QR Code® system 102 may encode data associated with a malfunction encountered during one or more operations of injection system 104 into one or more fields of the network resource. In some non-limiting embodiments, the network resource may include a plurality of fields. In one example, the network resource may include a first field for an identifier of injection system 104, a second field for an identifier of a service to which the network resource is to provide a link to, and a third field that includes data associated with injection system 104 that is pertinent to the service to which the network resource is to provide a link to. In such an example, the first field may include a model number or a serial number of injection system 104, the second field may include an identifier for a service that provides technical support for injection system 104, and the third field may include an error code associated with a malfunction encountered during operation of injection system 104.

In some non-limiting embodiments, QR Code® system 102 may encrypt one or more fields (e.g., into one or more values of one or more fields) of the network resource. For example, QR Code® system 102 may encrypt one or more fields of the network resource using a pretty good privacy (PGP) encryption technique. In some non-limiting embodiments, remote support system 108 may decrypt the one or more fields of the network resource that were encrypted. For example, remote support system 108 may decrypt the encrypted one or more fields of the network resource using the PGP encryption technique that was used to encrypt the encrypted one or more fields.

As further shown in FIG. 3A, at step 306, process 300 includes generating a quick response (QR) Code®. For example, QR Code® system 102 may generate the QR Code® based on the network resource. In some non-limiting embodiments, QR Code® system 102 may generate (e.g., automatically generate) the QR Code® based on generating the network resource. In some non-limiting embodiments, QR Code® system 102 may generate the QR Code® that is to be displayed on a display screen. For example, QR Code® system 102 may generate the QR Code® that is to be displayed as part of a graphical user interface (GUI), which is to be displayed on a display screen of injection system 104, workstation device 106, remote support system 108, and/or user device 110.

In some non-limiting embodiments, the QR Code® may include one or more static data elements associated with injection system 104 and/or one or more dynamic data elements associated with injection system 104. In some non-limiting embodiments, a static data element associated with injection system 104 may include a data element for which the value does not change following installation (e.g., an initial activation for carrying out fluid injection operations) of injection system 104. In some non-limiting embodiments, a dynamic data element associated with injection system 104 may include a data element for which the value changes following installation of injection system 104. In some non-limiting embodiments, a static data element may include data associated with an identifier of the injection system, such as a model number of injection system 104 or a serial number of injection system 104. In some non-limiting embodiments, dynamic data element may include data associated with one or more operations of the injection system, such as data associated with a malfunction encountered during one or more operations of injection system 104 and/or data associated with one or more operations of injection system 104.

In some non-limiting embodiments, QR Code® system 102 may generate the QR Code® so that, upon scanning the QR Code®, the QR Code® causes user device 110 to perform a function. For example, QR Code® system 102 may generate the QR Code® so that, upon scanning the QR Code®, the QR Code® causes user device 110 to open a web browser with a webpage based on the URL from which the QR Code® was generated. In another example, QR Code® system 102 may generate the QR Code® so that, upon scanning the QR Code®, the QR Code® causes user device 110 to synchronize data associated with injection system 104 with remote support system 108 when injection system 104 is not connected (e.g., is not connected via communication network 112) with remote support system 108. In yet another example, QR Code® system 102 may generate the QR Code® so that, upon scanning the QR Code®, the QR Code® causes user device 110 to register data associated with injection system 104 with remote support system 108 when injection system 104 is not connected (e.g., is not connected via communication network 112) with remote support system 108. In still another example, QR Code® system 102 may generate the QR Code® so that, upon scanning the QR Code®, the QR Code® causes user device 110 to transmit data associated with a malfunction encountered during an operation of injection system 104 to remote support system 108. In still another example, QR Code® system 102 may generate the QR Code® so that, upon scanning the QR Code®, the QR Code® causes user device 110 to produce a license file (e.g., a file of licensed features) for injection system 104 that is to be transmitted to remote support system 108. In still another example, QR Code® system 102 may generate the QR Code® so that, upon scanning the QR Code®, the QR Code® causes user device 110 to activate a warranty registration for injection system 104 with remote support system 108. In still another example, QR Code® system 102 may generate the QR Code® so that, upon scanning the QR Code®, the QR Code® causes user device 110 to transmit data associated with injection system 108 that is to be uploaded to remote support system 108.

In some non-limiting embodiments, QR Code® system 102 may generate the QR Code® based on a user profile. For example, QR Code® system 102 may generate the QR Code® based on a level of access associated with a user profile (e.g., a user profile of a user associated with user device 110). In some non-limiting embodiments, levels of access associated with user profiles may include a first level of access associated with a user profile for a field service engineer, a second level of access associated with a user profile for a service support personnel, a third level of access associated with a user profile for a purchaser (e.g., a user that purchased injection system 104), and a fourth level of access associated with a user profile for a sales representative (e.g., a distributor of injection system 104, a dealer of injection system 104, etc.). In some non-limiting embodiments, QR Code® system 102 may generate the QR Code® such that only a specified user profile associated with a specified level of access may be able to scan the QR Code® and access the network resource associated with the QR Code® (e.g., the network resource based on which the QR Code® was generated).

In some non-limiting embodiments, QR Code® system 102 may generate the QR Code® and one or more encryption keys for accessing the network resource associated with the QR Code®. For example, QR Code® system 102 may generate the QR Code® and a private encryption key of a public/private encryption key pair to allow a user to access (e.g., access services of) the network resource associated with the QR Code®. In some non-limiting embodiments, the private encryption key may provide access to injection system 104.

In some non-limiting embodiments, QR Code® system 102 may generate a first QR Code® and a second QR Code®. For example, QR Code® system 102 may generate a first QR Code® that is to be displayed as part of a GUI, which is to be displayed on a display screen of injection system 104, workstation device 106, and/or user device 110. Additionally, QR Code® system 102 may generate a second QR Code® that is to be displayed as part of a GUI, which is to be displayed on a display screen of remote support system 108. In some non-limiting embodiments, QR Code® system 102 may generate the first QR Code® and the second QR Code® such that the first QR Code® is the same as the second QR Code®. For example, QR Code® system 102 may generate the first QR Code® and the second QR Code® based on the same network resource.

As further shown in FIG. 3A, at step 308, process 300 includes displaying the QR Code® on a display screen. For example, QR Code® system 102 may display (e.g., cause to be displayed) the QR Code® on a display screen of injection system 104, workstation device 106, remote support system 108, and/or user device 110. In some non-limiting embodiments, QR Code® system 102 may display the QR Code® in a GUI that is displayed on a display screen of injection system 104, workstation device 106, remote support system 108, and/or user device 110.

In some non-limiting embodiments, user device 110 may read (e.g., scan) the QR Code®. For example, user device 110 may read the QR Code® using a reader device of user device 110, such as a camera. In some non-limiting embodiments, user device 110 may generate a message based on reading the QR Code®. For example, user device 110 may generate a short message service (SMS) message (e.g., a text message), and/or an e-mail message based on reading the QR Code®. In some non-limiting embodiments, the message may have a template that is to be populated with data associated with injection system 104 that is encoded in QR Code®. Additionally or alternatively, the message may have one or more fields for which a user may provide an input to populate the one or more fields. In some non-limiting embodiments, user device 110 may transmit (e.g., automatically transmit) the message based on reading the QR Code®. In some non-limiting embodiments, user device 110 may transmit the message based on receiving a user input.

In some non-limiting embodiments, user device 110 may perform (e.g., automatically perform) an action associated with a service associated with the network resource from which the QR Code® was generated based on reading the QR Code®. In one example, user device 110 may open a web browser with a webpage based on the network resource from which the QR Code® was generated based on reading the QR Code®. In another example, user device 110 may synchronize data associated with injection system 104 with remote support system 108 when injection system 104 is not connected (e.g., is not connected via communication network 112) with remote support system 108. In yet another example, user device 110 may register data associated with injection system 104 with remote support system 108 when injection system 104 is not connected (e.g., is not connected via communication network 112) with remote support system 108. In still another example, user device 110 may transmit data associated with a malfunction encountered during an operation of injection system 104 to remote support system 108. In still another example, user device 110 may produce a file (e.g., a license file) for injection system 104 that is to be transmitted to remote support system 108. In still another example, user device 110 may activate a warranty registration for injection system 104 with remote support system 108. In still another example, user device 110 may transmit data associated with injection system 104 that is to be uploaded to remote support system 108.

In some non-limiting embodiments, user device 110 may provide (e.g., transmit) data associated with user device 110, injection system 104, and/or workstation device 106 based on reading the QR Code®. For example, user device 110 may open a webpage based on the URL from which the QR Code® was generated based on reading the QR Code® and user device 110 may transmit location data associated with a location (e.g., GPS data associated with a location) of user device 110, injection system 104, and/or workstation device 106 via the webpage.

Referring now to FIG. 3B, FIG. 3B is a flowchart of an implementation 310 of a process (e.g., process 300) showing how a QR Code® may be generated, displayed, and scanned by a user (e.g., a user of user device 110).

Figure 4A:
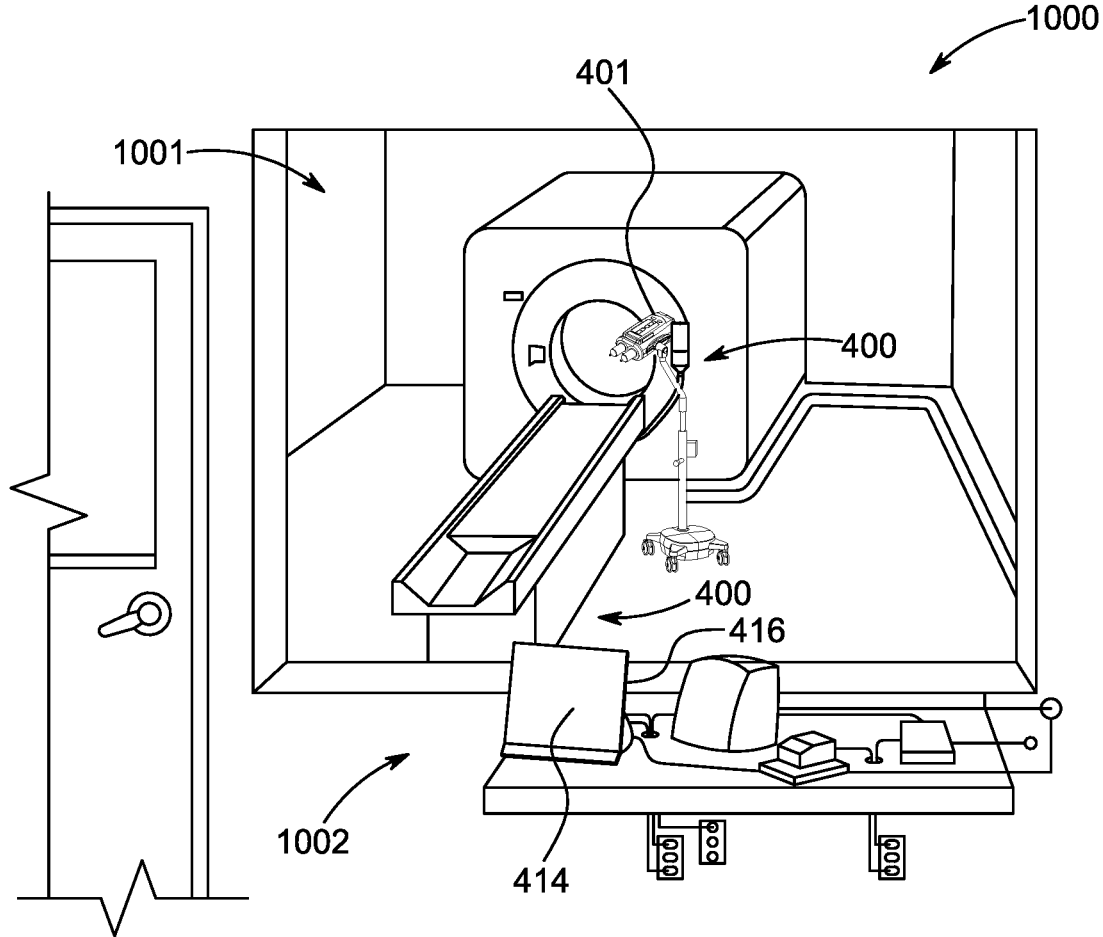
FIGS. 4A and 4B illustrate a non-limiting embodiment of a fluid injection system.
Figure 4B:
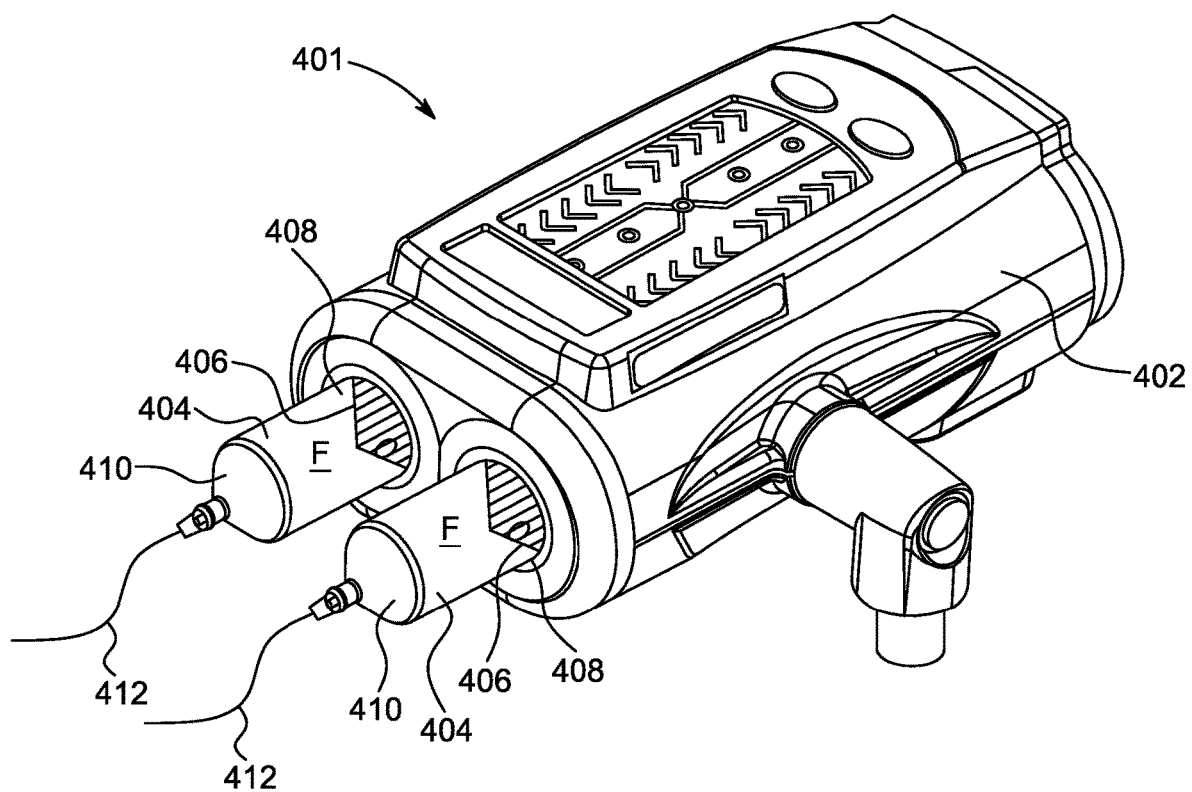

Referring now to FIGS. 4A and 4B, FIG. 4A illustrates a non-limiting embodiment of fluid injector system 400, such as the MEDRAD® Stellant Flex CT Injection System, located in a CT suite 1000. In some non-limiting embodiments, fluid injector system 400 may be the same or similar to injection system 104. As shown in FIG. 4A, fluid injector system 400 may include a bifurcated system that includes a scan room unit and a control room unit thereof located in the scan room 1001 and control room 1002, respectively, of CT suite 1000. In non-limiting embodiments, the scan room unit may include injector head unit 401 and the control room unit may include workstation 414, such as the Certegra® Workstation, with display screen 416. As shown in FIG. 4B, injector head unit 401 may include housing 402 and at least one fluid reservoir 404, such as a syringe or a fluid pump container. In some non-limiting embodiments, fluid injector system 400 may include, as best shown in FIG. 4B, a drive component to control fluid flow into or out of a fluid reservoir, such as a piston associated with each of fluid reservoirs 404 that drives plunger 406 within a barrel of fluid reservoir 404. In some non-limiting embodiments, each of fluid reservoirs 404 is adapted to releasably interface with housing 402 at port 408. Each fluid reservoir 404 of fluid injector system 400 is configured to be filled with at least one medical fluid F, such as an imaging contrast media, saline solution, or any desired medical fluid. Each fluid reservoir 404 may be filled with a different medical fluid F. In some non-limiting embodiments, fluid injector system 400 may be a multi-syringe injector, as shown, where several fluid reservoirs 404 may be oriented side-by-side or in another spatial relationship and are separately actuated by respective pistons associated with fluid injector system 400.

In some non-limiting embodiments, fluid injector system 400 may be used during a medical procedure to inject the at least one medical fluid F into the vasculature of a patient by driving plungers 406 associated with fluid reservoir 404 with a drive component. The drive component may move plunger 406 toward distal end 410 of fluid reservoir 404 to expel the fluid F from fluid reservoir 404 into and through fluid path set 412 during a priming, purging and/or fluid delivery step. In some non-limiting embodiments, fluid path set 412 may include at least one tube or tube set configured to be in fluid communication with each fluid reservoir 404 to place each fluid reservoir 404 in fluid communication with a flexible administration tube and associated catheter for delivering the fluid F from each fluid reservoir 404 to a patient at a vascular access site.

Figure 4C:
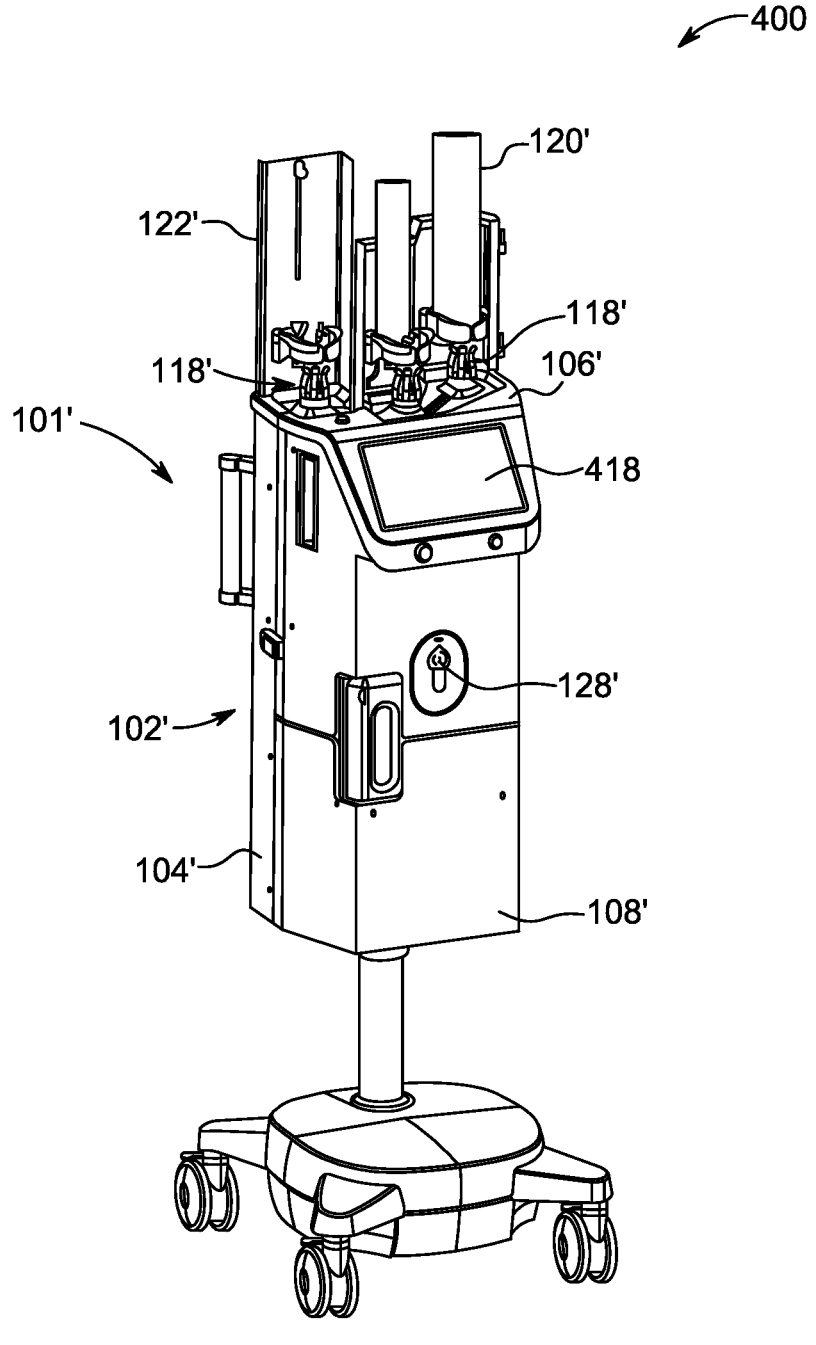
FIG. 4C illustrates another non-limiting embodiment of a fluid injection system.

Referring now to FIG. 4C, FIG. 4C illustrates another non-limiting embodiment of fluid injector system 400, namely a multi-fluid delivery system such as the MEDRAD® Centargo CT Injection System, with display screen 418. As shown in FIG. 4C, fluid injector system 400 may be configured to (e.g., adapted to) provide feedback about compliance with usage instructions. In some non-limiting embodiments, fluid injector system 400 includes powered fluid injector 101' connected to a fluid delivery set intended to be associated with an injector device to deliver fluids from one or more single-dose or multi-dose containers and fluid path sets under pressure into a patient. In some non-limiting embodiments, fluid injector 101' includes injector housing 102' with opposed lateral sides 104', distal or upper end 106', and proximal or lower end 108'. Injector housing 102' encloses the various mechanical drive components, electrical and power components necessary to drive the mechanical drive components, and control components, such as electronic memory and electronic control devices (hereinafter electronic control device(s)), used to control operation of reciprocally movable drive members, such as drive members associated with fluid injector system 400. Such drive members may be reciprocally operable via electro-mechanical drive components, such as a ball screw shaft driven by a motor, a voice coil actuator, a rack-and-pinion gear drive, a linear motor, and the like.

In some non-limiting embodiments, fluid injector system 400 may include at least one bulk fluid connector 118' for connection with at least one bulk fluid source 120'. Alternatively, the fluid source could be a single dose vial, rather than a bulk source. In some examples or aspects, a plurality of bulk fluid connectors 118' may be provided. In some non-limiting embodiments, three bulk fluid connectors 118' may be provided in a side-by-side or other arrangement. In some non-limiting embodiments, at least one bulk fluid connector 118' may be a spike configured for removably connecting to the at least one bulk fluid source 120', such as a vial, bottle, or a bag. The at least one bulk fluid connector 118' may have a reusable or non-reusable interface with each new bulk fluid source 120'. The at least one bulk fluid connector 118' may be formed on or attached by tubing with the multi-patient disposable set, as described herein. The at least one bulk fluid source 120' may be configured for receiving a medical fluid, such as saline, an imaging contrast solution, or other medical fluid, for delivery to fluid injector system 400. Injector housing 102' may have at least one support member 122' for supporting the at least one bulk fluid source 120' once it is connected to fluid injector system 400. In some non-limiting embodiments, fluid injector system 400 may include connection port 128'.

Figure 5:
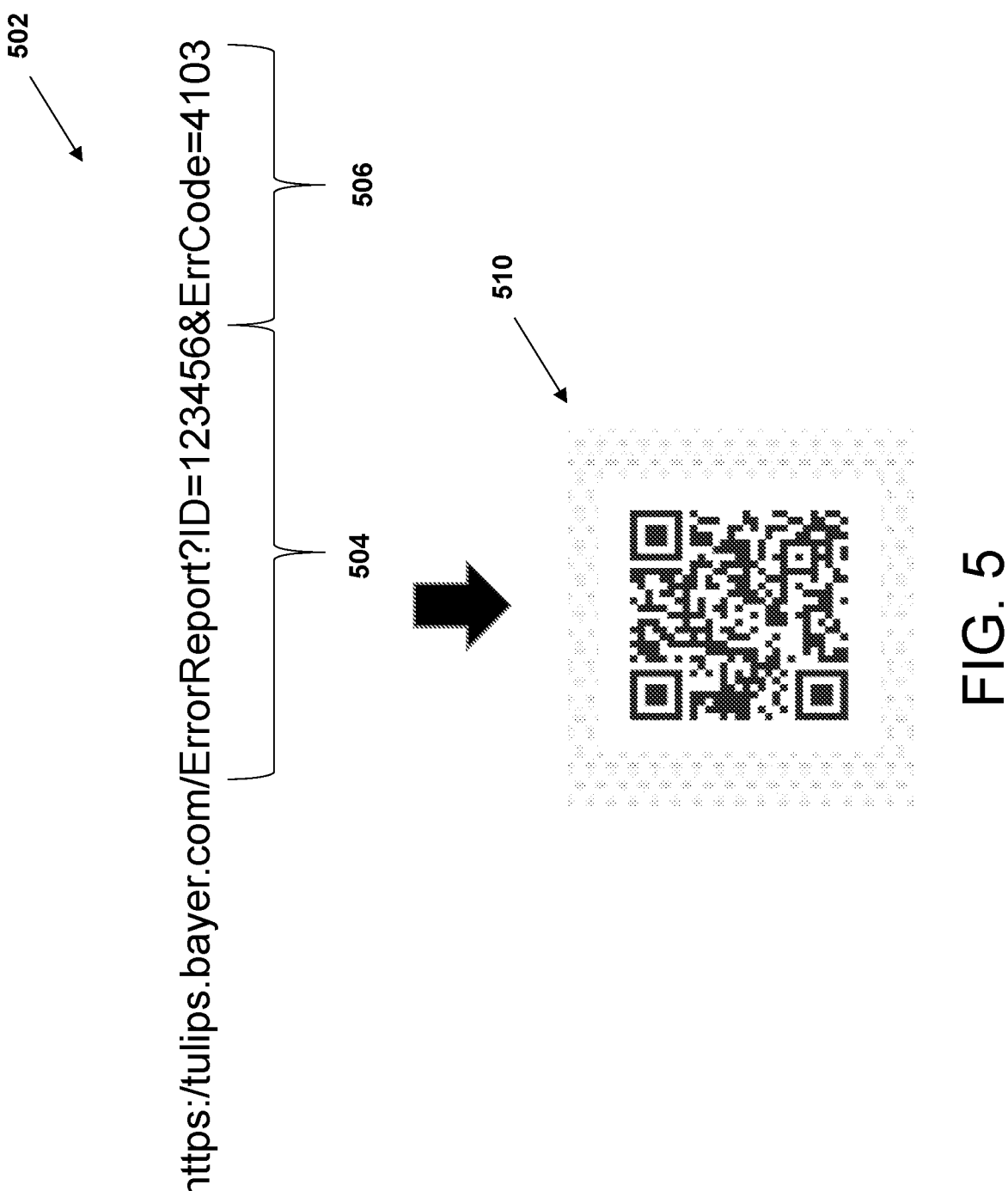
FIG. 5 is a diagram of a non-limiting embodiment of a uniform resource locator (URL) and a non-limiting embodiment of a QR Code®.

Referring now to FIG. 5, FIG. 5 is a diagram of URL 502 and QR Code® 510. As shown in FIG. 5, URL 502 may include a plurality of fields, and the plurality of fields may include data elements 504, 506. As further shown in FIG. 5, QR Code® 510 is generated based on the values of the plurality of fields of URL 502. In some non-limiting embodiments, data element 504 may include a static data element and data element 506 may include a dynamic data element. As shown in FIG. 5, data element 504 includes a static data element, which has a value of an identifier associated with injection system 104 for which an error report has been generated. As further shown in FIG. 5, data element 506 includes a dynamic data element, which has a value of an error code associated with a malfunction encountered during operation of injection system 104.

Figure 6:
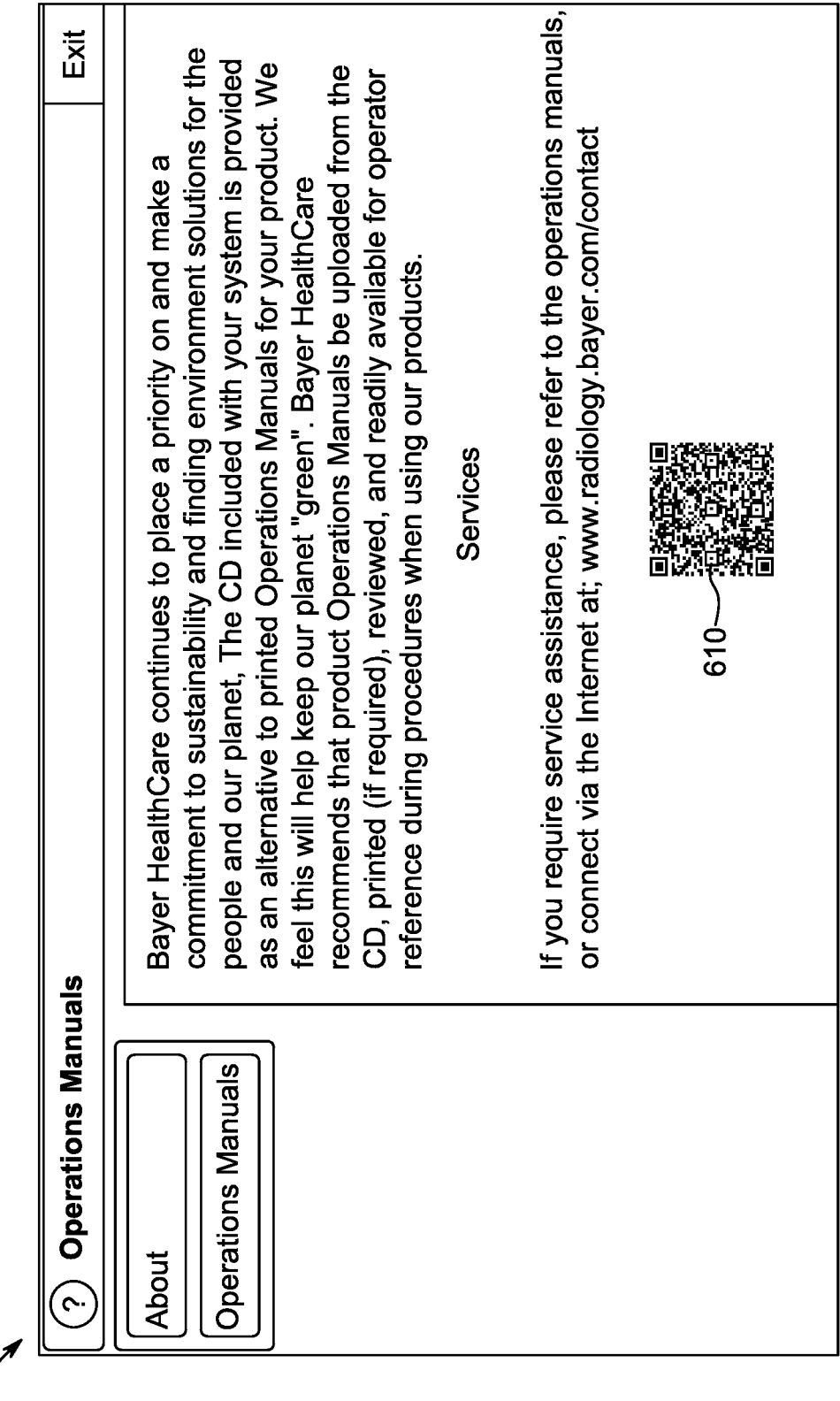
FIG. 6 is a diagram of a non-limiting embodiment of a graphical user interface that includes a QR Code®.

Referring now to FIG. 6, FIG. 6 is a diagram of GUI 600 that includes QR Code® 610. In some non-limiting embodiments, QR Code® 610 is the same or similar to QR Code® 510. As shown in FIG. 6, GUI 600 may be displayed on a display screen (e.g., a display screen of injection system 104 or a display screen of workstation device 106) to a user to provide the user with QR Code® 610 that allows the user to access a service associated with retrieving product documentation and/or equipment support services. Further, QR Code® 610 may also be encoded with a URL that includes a link to a website that allows the user to select and purchase a license to such an equipment support service or to obtain an upgrade of an existing license to an enhanced level of equipment support services. Examples of such support services offered by Bayer include VirtualCARE® Remote Support which permits secure and reliable remote monitoring of its contrast media injection systems and software to minimize downtime; SelectCARE®, PartnerCARE®, and DirectCARE® service agreement programs which offer increasing levels of service and capabilities including VirtualCARE®; TechCARE®; and TechCARE® NxT non-obsolescence programs which also include the services and capabilities offered through the enumerated service agreement programs.

Figure 7:
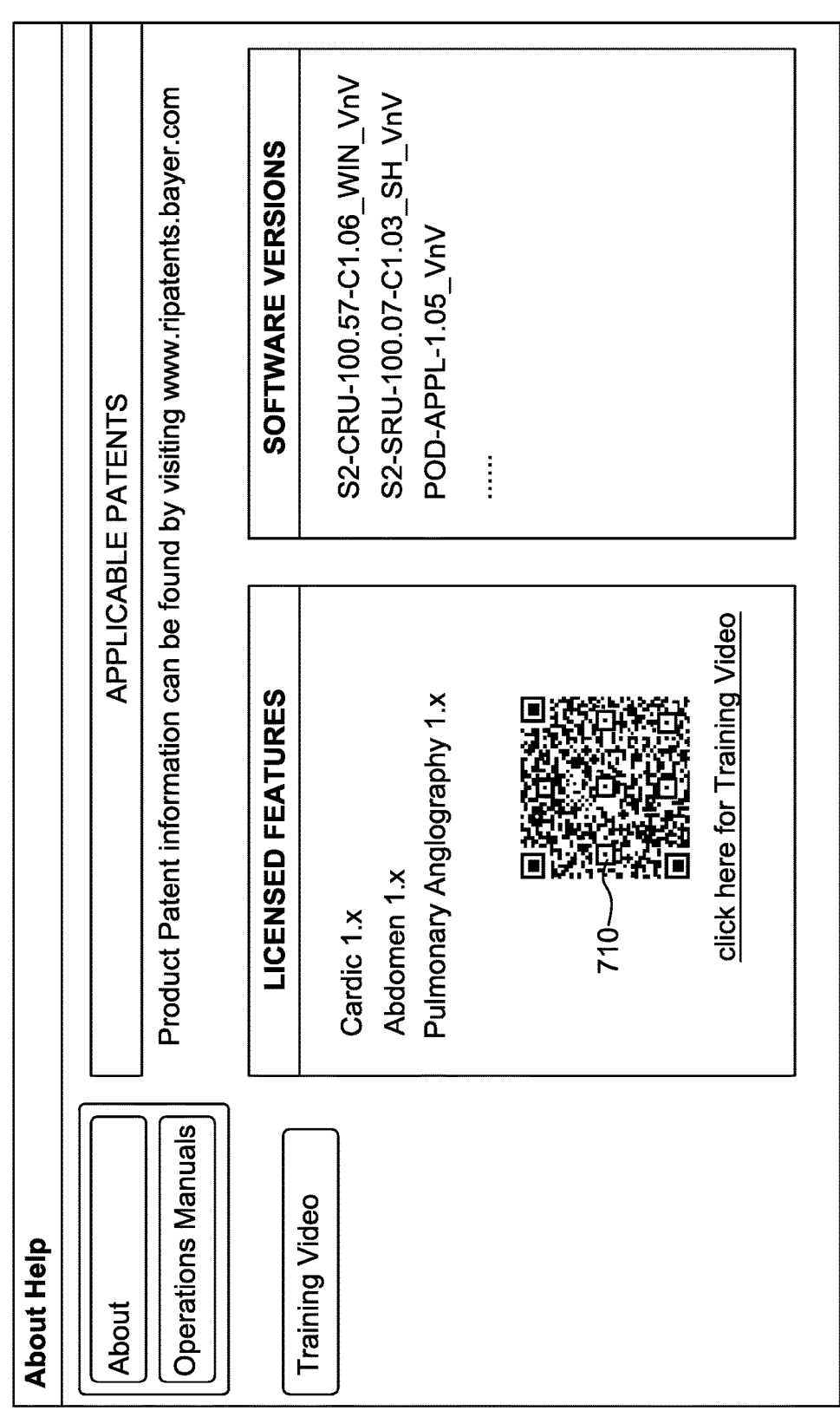
FIG. 7 is a diagram of a non-limiting embodiment of a graphical user interface that includes a QR Code®.

Referring now to FIG. 7, FIG. 7 is a diagram of GUI 700 that includes QR Code® 710. In some non-limiting embodiments, QR Code® 710 is the same or similar to QR Code® 510 and/or QR Code® 610. As shown in FIG. 7, GUI 700 may be displayed on a display screen (e.g., a display screen of injection system 104 or a display screen of workstation device 106) to a user to provide the user with QR Code® 710 that allows the user to access a service associated with retrieving product documentation and/or licensed features of injection system 104. An example of such a feature includes the Personalized Patient Protocol Technology (P3T) offered by Bayer. Allowing injection protocols to be automatically tailored to a patient, P3T® Software for Abdomen automates the calculation of injection protocols for CT imaging of the liver, pancreas, and kidneys based on contrast concentration and characteristics (e.g., weight) of the patient; P3T® Software for Cardiac automates the calculation of injection protocols for CT angiography of cardiac structures such as the coronary arteries, the aorta and chambers of the heart; and P3T® Software for Pulmonary Angiography allows personalization of injection protocols for CT angiography of the pulmonary vasculature.

Figure 8:
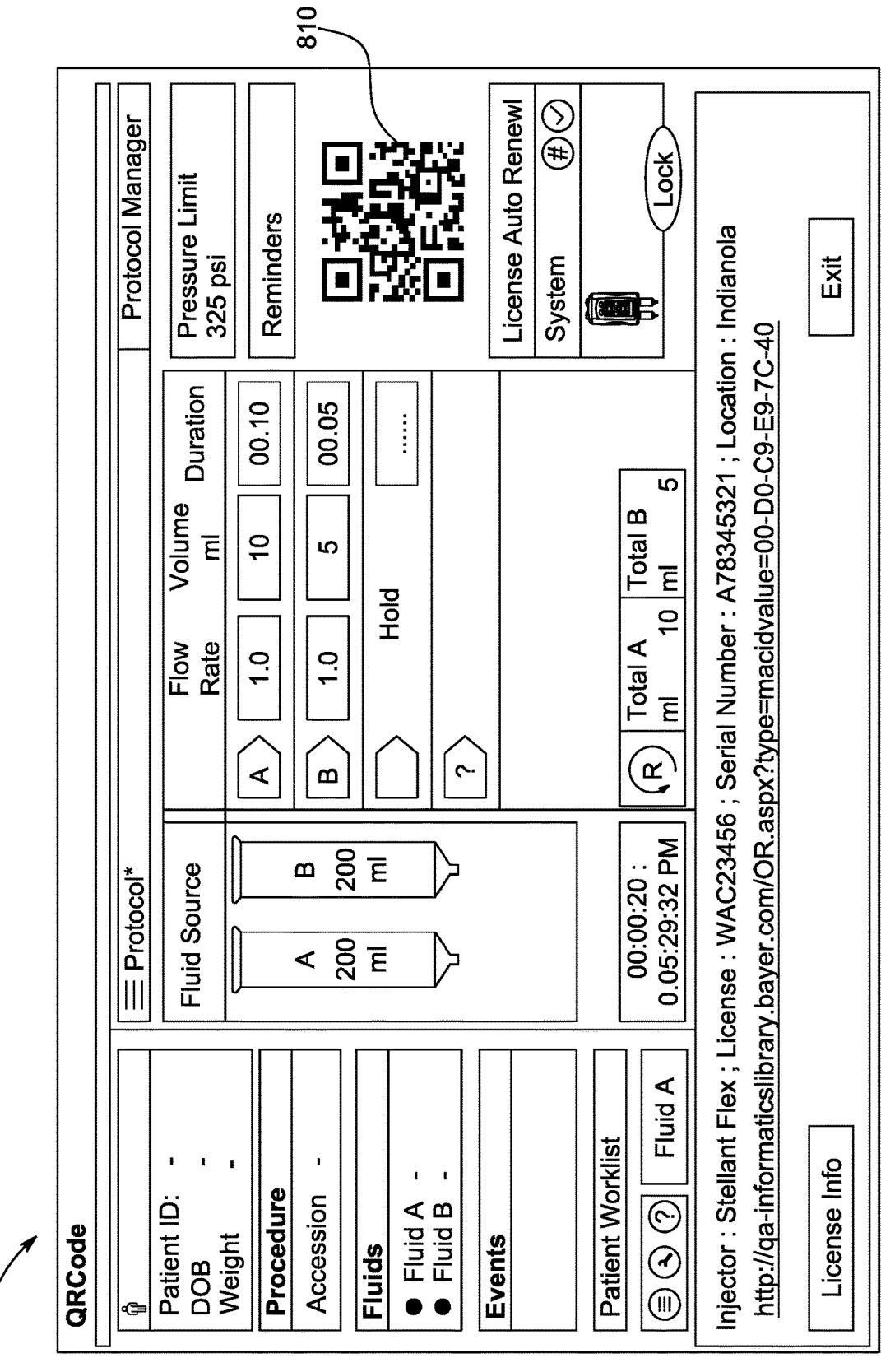
FIG. 8 is a diagram of a non-limiting embodiment of a graphical user interface that includes a QR Code®.

Referring now to FIG. 8, FIG. 8 is a diagram of GUI 800 that includes QR Code® 810. In some non-limiting embodiments, QR Code® 810 is the same or similar to QR Code® 510, QR Code® 610, and/or QR Code® 710. As shown in FIG. 8, GUI 800 may be displayed on a display screen (e.g., a display screen of injection system 104 or a display screen of workstation device 106) to a user to provide the user with QR Code® 810 that allows the user to access a service associated with renewing a license for features of injection system 104.

Referring now to FIG. 9, FIG. 9 is a diagram of GUI 900 that includes QR Code® 910. In some non-limiting embodiments, QR Code® 910 is the same or similar to QR Code® 510, QR Code® 610, QR Code® 710, and/or QR Code® 810. As shown in FIG. 9, GUI 900 may be displayed on a display screen (e.g., a display screen of injection system 104 or a display screen of workstation device 106) to a user to provide the user with QR Code® 910 that allows the user to access a service associated with equipment support services following a malfunction encountered during operation of injection system 104.

Although the present disclosure has been described in detail for the purpose of illustration based on what is currently considered to be the most practical and preferred embodiments or aspects, it is to be understood that such detail is solely for that purpose and that the present disclosure is not limited to the disclosed embodiments or aspects, but, on the contrary, is intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect.

What is claimed is:

1. An injection system for providing a matrix barcode comprising:

at least one processor programmed or configured to:

receive data associated with the injection system, wherein the data associated with the injection system comprises:

data associated with an identifier of the injection system, wherein the identifier comprises a model number of the injection system, a serial number of the injection system, or any combination thereof; and data associated with a malfunction encountered during one or more operations of the injection system;

automatically generate a network resource based on the data associated with the injection system, wherein the network resource comprises a uniform resource locator (URL), wherein, when automatically generating the network resource, the at least one processor is programmed or configured to:

remove sensitive data from the data associated with the injection system using a log scrubber;

encode the data associated with the malfunction encountered during one or more operations of the injection system and the data associated with an identifier of the injection system into the URL;

generate a plurality of encryption keys for accessing the URL;

encrypt one or more fields of the URL using a first encryption key of the plurality of encryption keys according to a pretty good privacy (PGP) encryption technique; and generate a matrix barcode based on the URL, wherein the matrix barcode comprises a two-dimensional barcode, and wherein the matrix barcode comprises a static data element and a dynamic data element, wherein the static data element comprises a first data element having a value that does not change following an initial activation of the injection system, wherein the first data element comprises the data associated with the identifier of the injection system, and wherein the dynamic data element comprises a second data element having a value that changes following an initial activation of the injection system, wherein the second data element comprises the data associated with the malfunction encountered during one or more operations of the injection system, and wherein the matrix barcode is configured to cause a user device to transmit the data associated with the malfunction encountered during one or more operations of the injection system and the data associated with the identifier of the injection system to a remote support system when the user device scans the matrix barcode; and display the matrix barcode on a graphical user interface (GUI) displayed on a display screen of the injection system; and the user device configured to:

scan the matrix barcode on the GUI displayed on the display screen of the injection system; and transmit the data associated with the malfunction encountered during one or more operations of the injection system and the data associated with the identifier of the injection system to the remote support system based on scanning the matrix barcode, wherein, when transmitting the data associated with the malfunction encountered during one or more operations of the injection system and the data associated with the identifier of the injection system to the remote support system, the user device is configured to:

open a webpage based on the URL from which the matrix barcode was generated based on scanning the matrix barcode; and transmit location data associated with a location of user device and the data associated with a malfunction encountered during one or more operations of the injection system and the data associated with an identifier of the injection system via the webpage;

the remote support system configured to:

decrypt the encrypted one or more fields of the network resource using a second encryption key of the plurality of encryption keys according to the PGP encryption technique that was used to encrypt the encrypted one or more fields.

2. The injection system of claim 1, wherein the at least one processor is further programmed or configured to:

log the data associated with the malfunction encountered during one or more operations of the injection system.

3. The injection system of claim 1, wherein the data associated with the injection system further comprises:

a software version of the injection system;

a revision number of software of the injection system;

an identifier of one or more software patches that have been applied to the injection system;

a media access control (MAC) address of a network interface controller (NIC) of the injection system;

an identifier of an error associated with an operation of the injection system; or any combination thereof; and wherein the at least one processor is further programmed or configured to:

encode, into the URL, at least one of the following:

the software version of the injection system;

the revision number of software of the injection system;

the identifier of one or more software patches that have been applied to the injection system;

the MAC address of the NIC of the injection system; or the identifier of the error associated with the operation of the injection system.

4. A system for providing a matrix barcode associated with an injection system comprising:

the injection system; and at least one processor in communication with the injection system, wherein the at least one processor is programmed or configured to:

receive data associated with the injection system, wherein the data associated with the injection system comprises:

data associated with an identifier of the injection system, wherein the identifier comprises a model number of the injection system, a serial number of the injection system, or any combination thereof; and data associated with a malfunction encountered during one or more operations of the injection system;

automatically generate a network resource based on the data associated with the injection system, wherein the network resource comprises a uniform resource locator (URL), wherein, when automatically generating the network resource, the at least one processor is programmed or configured to:

remove sensitive data from the data associated with the injection system using a log scrubber;

encode the data associated with the malfunction encountered during one or more operations of the injection system and the data associated with the identifier of the injection system into the URL;

generate a plurality of encryption keys for accessing the URL;

encrypt one or more fields of the URL using a first encryption key of the plurality of encryption keys according to a pretty good privacy (PGP) encryption technique; and generate the matrix barcode based on the URL, wherein the matrix barcode comprises a two-dimensional barcode, and wherein the matrix barcode comprises a static data element and a dynamic data element, wherein the static data element comprises a first data element having a value that does not change following an initial activation of the injection system, wherein the first data element comprises the data associated with the identifier of the injection system, and wherein the dynamic data element comprises a second data element having a value that changes following an initial activation of the injection system, wherein the second data element comprises the data associated with the malfunction encountered during one or more operations of the injection system, and wherein the matrix barcode is configured to cause a user device to transmit the data associated with the malfunction encountered during one or more operations of the injection system and the data associated with the identifier of the injection system to a remote support system when the user device scans the matrix barcode; and display the matrix barcode on a graphical user interface (GUI) displayed on a display screen of the injection system;

the user device configured to:

scan the matrix barcode on the GUI displayed on the display screen of the injection system; and transmit the data associated with the malfunction encountered during one or more operations of the injection system and the data associated with the identifier of the injection system to the remote support system based on scanning the matrix barcode, wherein, when transmitting the data associated with the malfunction encountered during one or more operations of the injection system and the data associated with the identifier of the injection system to the remote support system, the user device is configured to:

open a webpage based on the URL from which the matrix barcode was generated based on scanning the matrix barcode; and transmit location data associated with a location of user device and the data associated with the malfunction encountered during one or more operations of the injection system and the data associated with the identifier of the injection system via the webpage;

the remote support system configured to:

decrypt the encrypted one or more fields of the network resource using a second encryption key of the plurality of encryption keys according to the PGP encryption technique that was used to encrypt the encrypted one or more fields.

5. The system of claim 4, wherein the at least one processor is further programmed or configured to:

log the data associated with the malfunction encountered during one or more operations of the injection system.

6. The system of claim 4, wherein the data associated with the injection system further comprises:

a software version of the injection system;

a revision number of software of the injection system;

an identifier of one or more software patches that have been applied to the injection system;

a media access control (MAC) address of a network interface controller (NIC) of the injection system;

an identifier of an error associated with an operation of the injection system; or any combination thereof; and wherein the at least one processor is further programmed or configured to:

encode, into the URL, at least one of the following:

the software version of the injection system;

the revision number of software of the injection system;

26 the identifier of one or more software patches that have been applied to the injection system;

the MAC address of the NIC of the injection system; or the identifier of the error associated with the operation of the injection system.

7. A computer program product for providing a matrix barcode associated with an injection system, the computer program product comprising at least one non-transitory computer-readable medium comprising one or more instructions that, when executed by at least one processor of the injection system, cause the at least one processor to:

receive data associated with the injection system, wherein the data associated with the injection system comprises:

data associated with an identifier of the injection system, wherein the identifier comprises a model number of the injection system, a serial number of the injection system, or any combination thereof; and data associated with a malfunction encountered during one or more operations of the injection system;

automatically generate a network resource based on the data associated with the injection system, wherein the network resource comprises a uniform resource locator (URL), wherein, the one or more instructions that cause the at least one processor to automatically generate the network resource, cause the at least one processor to:

remove sensitive data from the data associated with the injection system using a log scrubber;

encode the data associated with a malfunction encountered during one or more operations of the injection system and the data associated with the identifier of the injection system into the URL;

generate a plurality of encryption keys for accessing the URL;

encrypt one or more fields of the URL using a first encryption key of the plurality of encryption keys according to a pretty good privacy (PGP) encryption technique; and generate the matrix barcode based on the URL, wherein the matrix barcode comprises a two-dimensional barcode, and wherein the matrix barcode comprises a static data element and a dynamic data element, wherein the static data element comprises a first data element having a value that does not change following an initial activation of the injection system, wherein the first data element comprises the data associated with the identifier of the injection system, and wherein the dynamic data element comprises a second data element having a value that changes following the initial activation of the injection system, wherein the second data element comprises the data associated with the malfunction encountered during one or more operations of the injection system, and wherein the matrix barcode is configured to cause a user device to transmit the data associated with the malfunction encountered during one or more operations of the injection system and the data associated with the identifier of the injection system to a remote support system when the user device scans the matrix barcode; and display the matrix barcode on a graphical user interface (GUI) displayed on a display screen of the injection system;

wherein the at least one non-transitory computer-readable medium further comprising one or more instructions that, when executed by the user device, cause the user device to:

scan the matrix barcode on the GUI displayed on the display screen of the injection system; and transmit the data associated with a malfunction encountered during one or more operations of the injection system and the data associated with the identifier of the injection system to the remote support system based on scanning the matrix barcode, wherein, the one or more instructions that cause the user device to transmit the data associated with the malfunction encountered during one or more operations of the injection system and the data associated with the identifier of the injection system to the remote support system, cause the user device to:

open a webpage based on the URL from which the matrix barcode was generated based on scanning the matrix barcode; and transmit location data associated with a location of user device and the data associated with the malfunction encountered during one or more operations of the injection system and the data associated with the identifier of the injection system via the webpage;

wherein the at least one non-transitory computer-readable medium further comprising one or more instructions that, when executed by the remote support system, cause the remote support system to:

decrypt the one or more encrypted fields of the network resource using a second encryption key of the plurality of encryption keys according to the PGP encryption technique that was used to encrypt the encrypted one or more fields.

8. The computer program product of claim 7, wherein the one or more instructions further cause the at least one processor to:

log the data associated with the malfunction encountered during one or more operations of the injection system.

9. The computer program product of claim 7, wherein the data associated with the injection system further comprises:

a software version of the injection system;

a revision number of software of the injection system;

an identifier of one or more software patches that have been applied to the injection system;

a media access control (MAC) address of a network interface controller (NIC) of the injection system;

an identifier of an error associated with an operation of the injection system; or any combination thereof; and wherein the one or more instructions further cause the at least one processor to:

encode, into the URL, at least one of the following:

the software version of the injection system;

the revision number of software of the injection system;

the identifier of one or more software patches that have been applied to the injection system;

the MAC address of the NIC of the injection system; or the identifier of the error associated with the operation of the injection system.

* * * * *